(12) United States Patent
Daly

(10) Patent No.: US 7,851,652 B2
(45) Date of Patent: Dec. 14, 2010

(54) BIOLOGICAL BUFFERS WITH WIDE BUFFERING RANGES

(76) Inventor: Thomas Daly, 914 S. Mitchell Ave., Arlington Heights, IL (US) 60005

( * ) Notice: Subject to any disclaimer, the term of this patent is extended or adjusted under 35 U.S.C. 154(b) by 0 days.

(21) Appl. No.: 12/437,749

(22) Filed: May 8, 2009

(65) Prior Publication Data

US 2009/0264651 A1 Oct. 22, 2009

Related U.S. Application Data

(63) Continuation-in-part of application No. 12/151,899, filed on May 9, 2008, now Pat. No. 7,635,791.

(60) Provisional application No. 61/124,586, filed on Apr. 17, 2008, provisional application No. 61/135,058, filed on Jul. 16, 2008.

(51) Int. Cl.
C07C 229/08 (2006.01)
(52) U.S. Cl. .................................... 562/567
(58) Field of Classification Search ........................ None
See application file for complete search history.

(56) References Cited

U.S. PATENT DOCUMENTS

| 3,562,273 | A | 2/1971 | Salat et al. |
|---|---|---|---|
| 4,112,050 | A | 9/1978 | Sartori et al. |
| 4,277,244 | A | 7/1981 | Bugaut et al. |
| 4,328,143 | A | 5/1982 | Izumi et al. |
| 4,719,049 | A | 1/1988 | Bair |
| 4,910,303 | A | 3/1990 | Su et al. |
| 5,051,212 | A | 9/1991 | Culshaw et al. |
| 5,350,837 | A | 9/1994 | Bridger et al. |
| 6,251,908 | B1 | 6/2001 | Bottcher et al. |
| 6,326,187 | B1 | 12/2001 | Jones et al. |

OTHER PUBLICATIONS

Database CAPLUS on STN, Acc. No. 1945:28500, Cook et al., Journal of the Chemical Society (1945), p. 399-402 (abstract).*
Database CAPLUS on STN, Acc. No. 1945:28452, J. Org. Chem. (1945), 10, p. 243-254 (abstract).
Database CAPLUS on STN, Acc. No. 1977:96787, Bulletin de la Societe Chimique de France (1975), 5-6, Pt.2, p. 1155-1159 (abstract).
Database CAPLUS on STN, Acc. No. 1952:14360, J. Am. Chem. Soc. (1951), 73, p. 2595-2596 (abstract).
Database CAPLUS on STN, Acc. No. 1989:597338, EP 317542 (May 24, 1989) (abstact).
Database CAPLUS on STN, Acc. No. 1970:473647, Acta Biologica et Medica Germanica (1970), 24(1-2), p. 189-200 (abstract).
Database CAPLUS on STN, Acc. No. 1994:49593, EP 569132 (Nov. 10, 1993) (abstract).
Database CAPLUS on STN, Acc. No. 1981:463826, DE 3040729 (May 14, 1981) (abstract).
Database CAPLUS on STN, Acc. No. 1970:495314, Science (1970), 169(3940), p. 97-98 (abstract).
Norman E. Good, "Uncoupling of the Hill Reaction from Photoposphorylation by Anions", Archives of Biochem & BioPhys 96, 653-661, (1962).
Norman E. Good et al., "Hydrogen Ion Buffers for Biological Research", Biochemistry 5(2) 467-477 (1966).
Angus Chemical Co. Technical Bulletin IB 69: Tris(Hydroxymethyl)Aminomethane (Tris Amino Reg TM) Cas 77-86-1 (2000).
Angus Chemical Co. Technical Bulletin IDS 10: Primary Amino Alcohols. (2000).
Angus Chemical Co. Technical Bulletin IDS 15: Nitro Alcohols. (2000).
International Search Report and Written Opinion PCT/US09/43291, Jul. 31, 2009.
International Search Report and Written Opinion PCT/US09/43291, (mailed Jul. 31, 2009).

* cited by examiner

Primary Examiner—Brian J Davis
(74) Attorney, Agent, or Firm—Clifford Kraft

(57) ABSTRACT

Amines and amine derivatives that improve the buffering range, and/or reduce the chelation and other negative interactions of the buffer and the system to be buffered. The reaction of amines or polyamines with various molecules to form polyamines with differing pKa's will extend the buffering range, derivatives that result in polyamines that have the same pKa yields a greater buffering capacity. Derivatives that result in zwitterionic buffers improve yield by allowing a greater range of stability.

9 Claims, 38 Drawing Sheets

BIOLOGICAL BUFFERS WITH WIDE BUFFERING RANGES

This application is a continuation in part of application Ser. No. 12/151,899 filed May 9, 2008 now U.S. Pat. No. 7,635, 791. That application claimed priority from U.S. Provisional Patent application No. 61/124,586 file Apr. 17, 2008. This application also claims priority from U.S. Provisional Patent application No. 61/135,058 filed Jul. 16, 2008. Application Ser. Nos. 12/151,899, 61/135,058 and 61/124,586 are hereby incorporated by reference.

BACKGROUND

1. Field of the Invention

The present invention relates generally to the field of amines and more particularly to a classes of amines used as buffers in biological systems.

2. Description of the Problem Solved by the Invention

Amines are very useful compounds in the buffering of biological systems. Each class of amine has various limitations which require choosing an amine based on multiple factors to select the best amine. For example, pH buffering range is typically most important, but issues of chelation, and pH range stability, and solubility also come into play. Typically, a suboptimal buffer will result in yields that are well below the potential yield. The invention disclosed improves the yields in fermentation and purification, and improves shelf stability of proteins and amino acids.

SUMMARY OF THE INVENTION

The present invention relates to amines and amine derivatives that improve the buffering range, and/or reduce the chelation and other negative interactions of the buffer and the system to be buffered. The reaction of amines or polyamines with various molecules to form polyamines with differing pKa's will extend the buffering range, derivatives that result in polyamines that have the same pKa yields a greater buffering capacity. Derivatives that result in zwitterionic buffers improve yield by allowing a greater range of stability.

DESCRIPTION OF THE FIGURES

Attention is now directed to the following figures that describe embodiments of the present invention:

FIG. 9 shows alkoxylation of aminomethylpropanol.

FIG. 12 shows the synthesis of a series of buffers with 1-nitropropane as a starting material where n and m are integers where m+n is greater than zero and n is greater than or equal to m.

Several drawings and illustrations have been presented to aid in understanding the invention. The scope of the present invention is not limited to what is shown in the figures.

DETAILED DESCRIPTION OF THE INVENTION

Combining amines with monochloroacetic acid (MCA) or sodium vinyl sulfonate (SVS) results in products are zwitterionic buffers that can buffer in both acidic and basic pH conditions. A limited number amines are currently used for this purpose, such as, tromethamine and ammonia. The reaction of amines, alcohols, and aminoalcohols with acrylonitrile (via the Michaels Addition), followed by reduction results in amines and polyamines that have a broad buffering range. The further derivatization of the amines and polyamines with MCA and SVS yields a further crop of amine buffers with desirable properties. MCA and sodium monochloroacetic acid (SMCA) can be used interchangeably.

The reaction of tromethamine as described above yields the products in FIG. 1. In step 1 in FIG. 1 where the acrylonitrile is added to the amine a branched structure wherein the addition of acrylonitrile results in a tertiary amine is shown. In reality, particularly when n is greater than 1, a mixture of products is obtained that is both tertiary and secondary. For the invention disclosed herein, n may equal any integer greater than zero, including 1. Controlling the reaction temperature, pressure and agitation will allow the mixture to be predominately secondary (such as when m=n) or tertiary amine, m can be any integer less than or equal n. Furthermore, this selection can take place in adding acrylonitrile to the amine that results, allowing a progressively more branched product. It is within the scope of the invention disclosed herein to include these additional types of products and their subsequent derivatives described herein.

Figure 1:
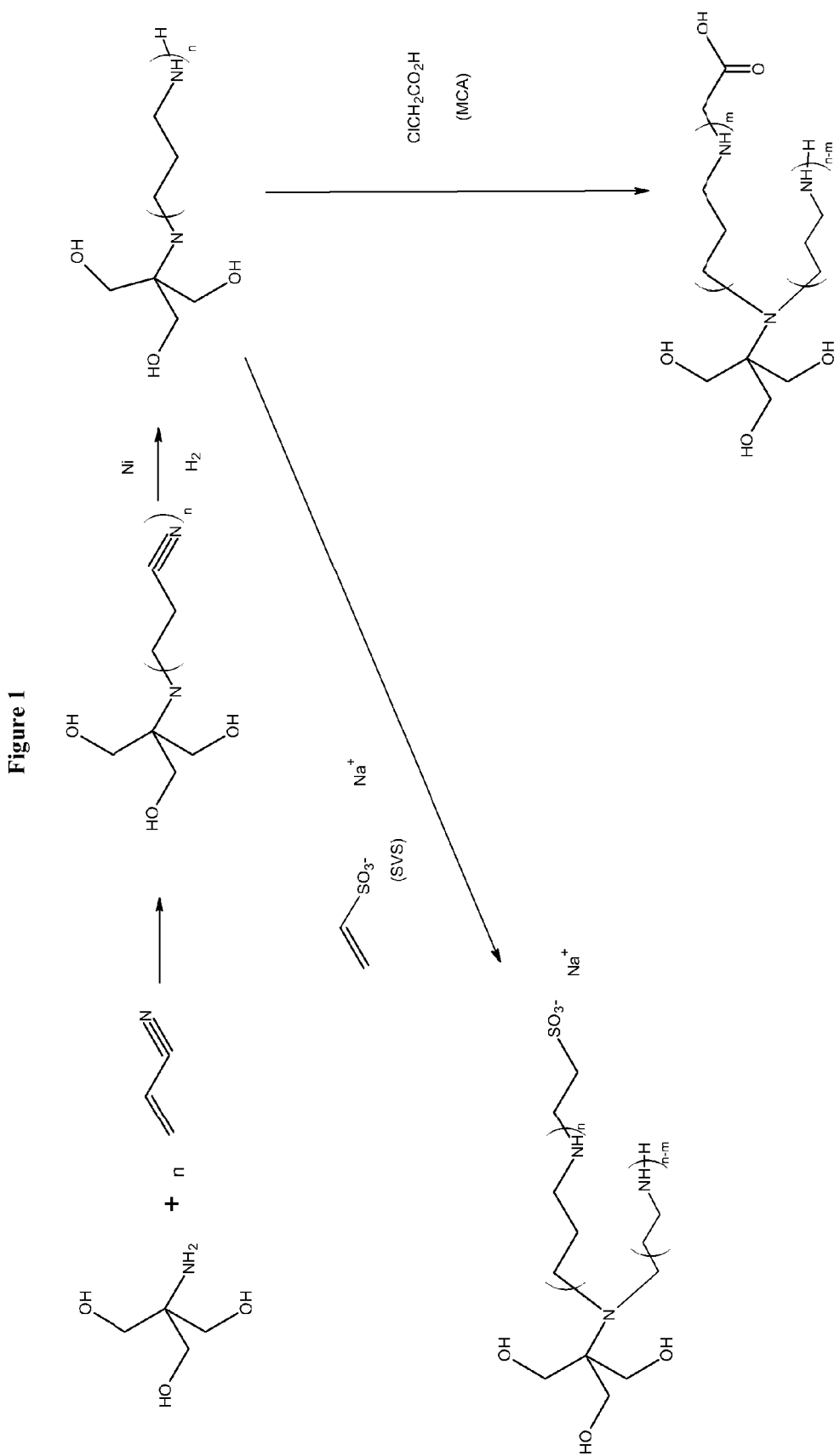
FIG. 1 shows the derivation of polyamines and zwitterionic buffers from tromethamine.

With regard to the reaction of the polyamine resulting from the second step in FIG. 1. FIG. 1 shows the addition of only one mole of SVS or MCA, it is known in the art, that a second mole may be added to obtain a product with a second zwitterionic group. Furthermore, in the case where the product has repeated additions of acrylonitrile and reduction to the amines, the branched products may have many more zwitterionic groups. Also, it is to be noted that, while the sulfonates are shown as sodium salts, other salts and the free acids (non-salted form) are also within the scope of this invention.

Other amines that would make excellent starting materials in place of tromethamine are 2-amino-2-methyl-1-propanol, 2-amino-1-butanol, 2-amino-2-ethyl-1,3-propanediol, 2-amino-2-methyl-1,3-propanediol, and dihydroxymethylaminomethane.

Additionally, fatty amines, such as lauryl amine, coco amine, tallow amine, and oleoyl amine, and fatty ether amines, such as bis-(2-hydroxyethyl)isodecyloxypropylamine, when reacted with SVS produce mild surfactants that find utility where zwitterionic surfactants are desired, including personal care.

Figure 2:
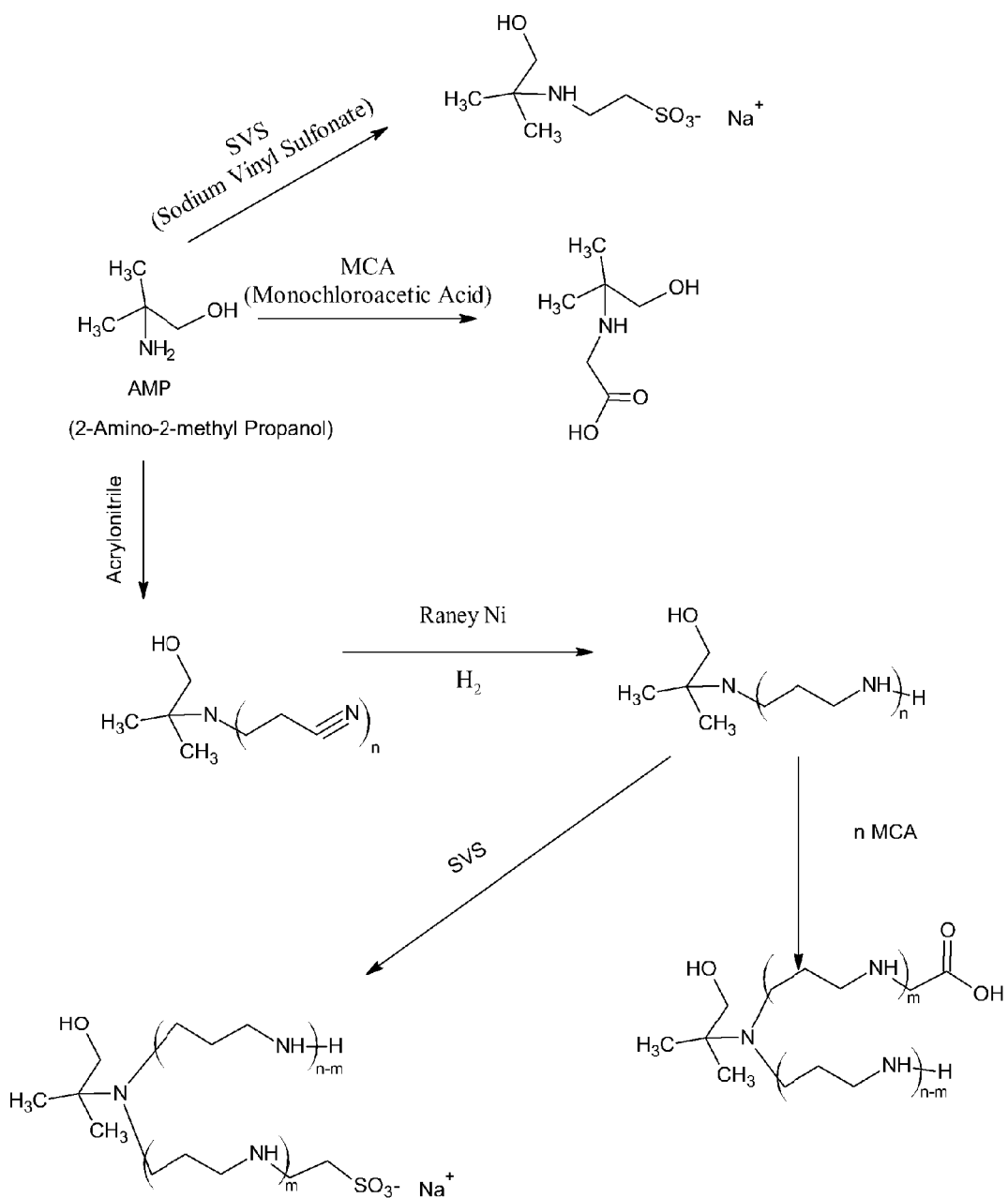
FIG. 2 shows the derivation of zwitterionic buffers and polyamines from aminomethylpropanol.

Other amines that are shown in FIG. 2 are produced via a similar series of reactions, except that FIG. 2 includes zwitterionic buffers from the amine 2-amino-2-methyl-1-propanol, as well as the polyamines derived from the reaction with acrylonitrile and the subsequent derivatives described above. Other amines can be utilized in addition to 2-amino-2-methyl-1-propanol to obtain excellent buffers are 2-amino-1-butanol, 2-amino-2-ethyl-1,3-propanediol, 2-amino-2-methyl-1,3-propanediol, and dihydroxymethylaminomethane. Reaction conditions could be created such that the alcohol groups on the amines listed above could be reacted with acrylonitrile as well, and then reduced to the amines and, if desired, reacted with SVS or MCA to impart zwitterionic character.

Polyamines with good properties for use in biological fermentations, purifications, storage and general handling can also be produced through the reaction of nitroalcohols and acrylonitrile, followed by reduction. Additional derivatization with SVS or MCA will result in zwitterionic buffers with a very large buffering range and capacity.

Figure 3:
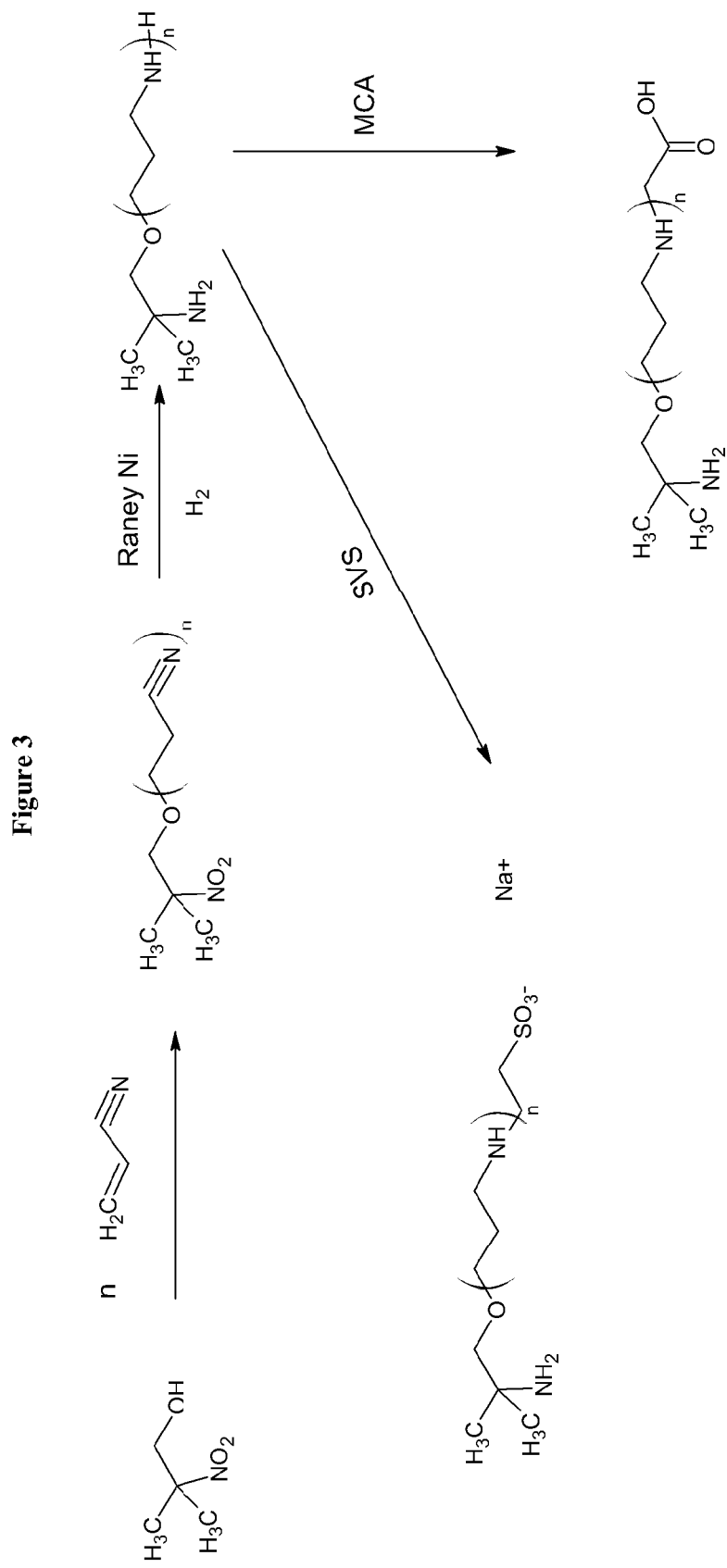
FIG. 3 shows the reaction of 2-methyl-2-nitro-1-propanol with acrylonitrile and its derivatives.

FIG. 3 shows the reaction of 2-methyl-2-nitro-1-propanol with acrylonitrile and its derivatives.

Figure 4:
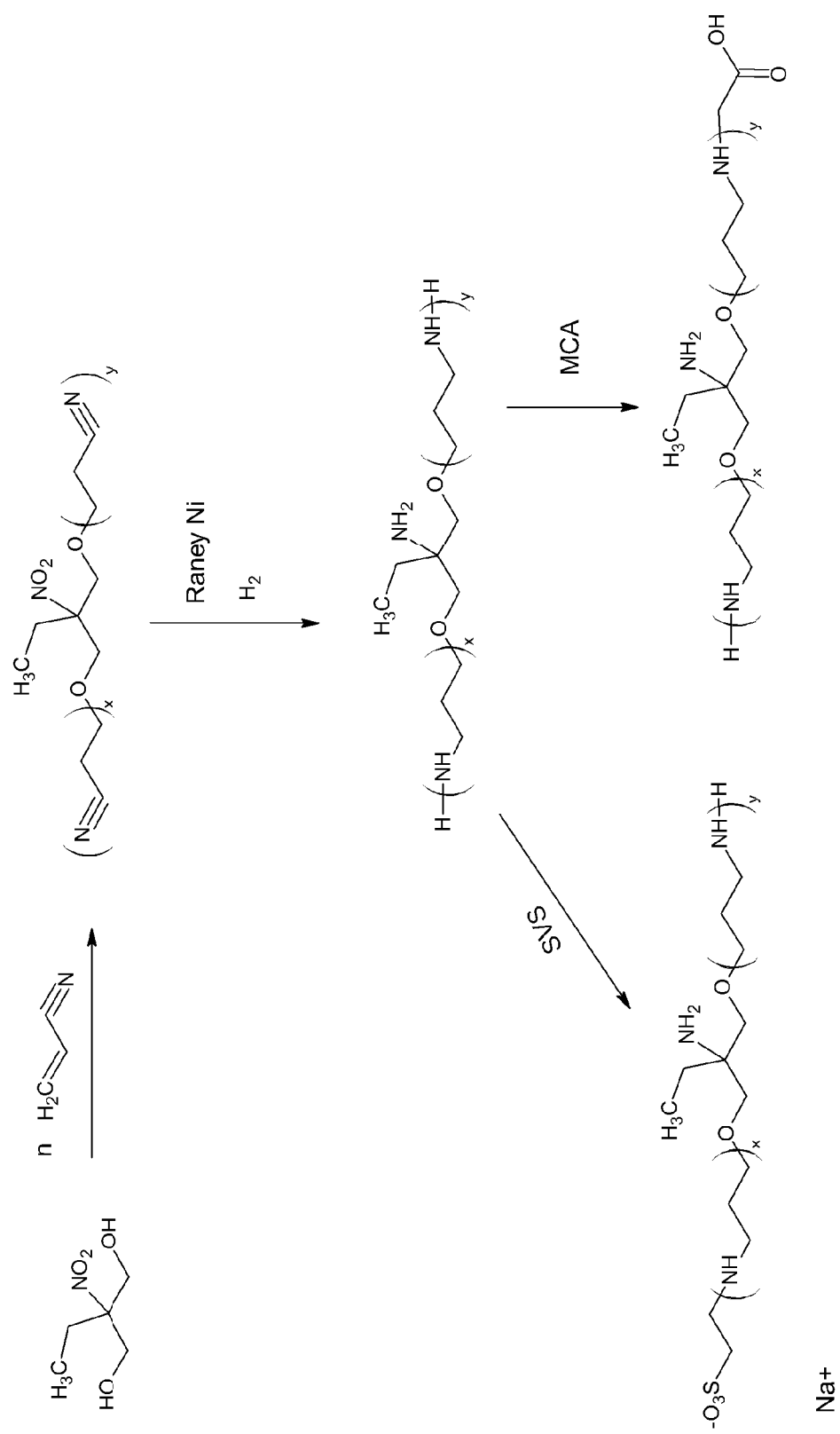
FIG. 4 shows the reaction of 2-nitro-2-ethyl-1,3-propanediol with acrylonitrile and its derivatives where x, y, and n are all integers where x and y are chosen independently, such that x+y=n and n is greater than zero.

FIG. 4 shows the reaction of 2-nitro-2-ethyl-1,3-propanediol with acrylonitrile and its derivatives where x, y, and n are all integers where x and y are chosen independently, such that x+y=n and n is greater than zero.

Figure 5:
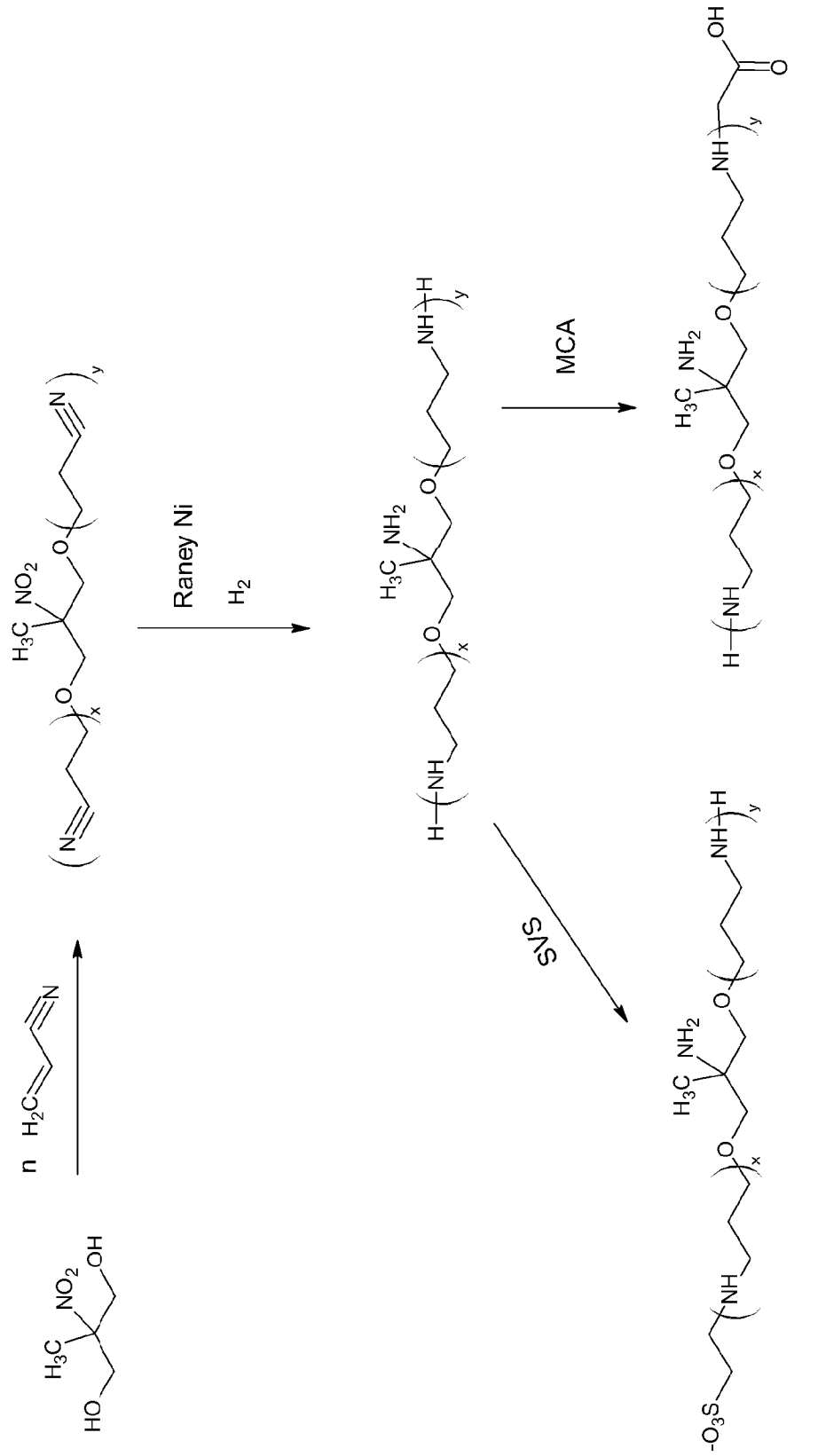
FIG. 5 shows the reaction of 2-nitro-2-methyl-1,3-propanediol with acrylonitrile and its derivatives where x, y, and n are all integers where x and y are chosen independently, such that x+y=n and n is greater than zero.

FIG. 5 shows the reaction of 2-nitro-2-methyl-1,3-propanediol with acrylonitrile and its derivatives where x, y, and n are all integers where x and y are chosen independently, such that x+y=n and n is greater than zero.

Figure 6:
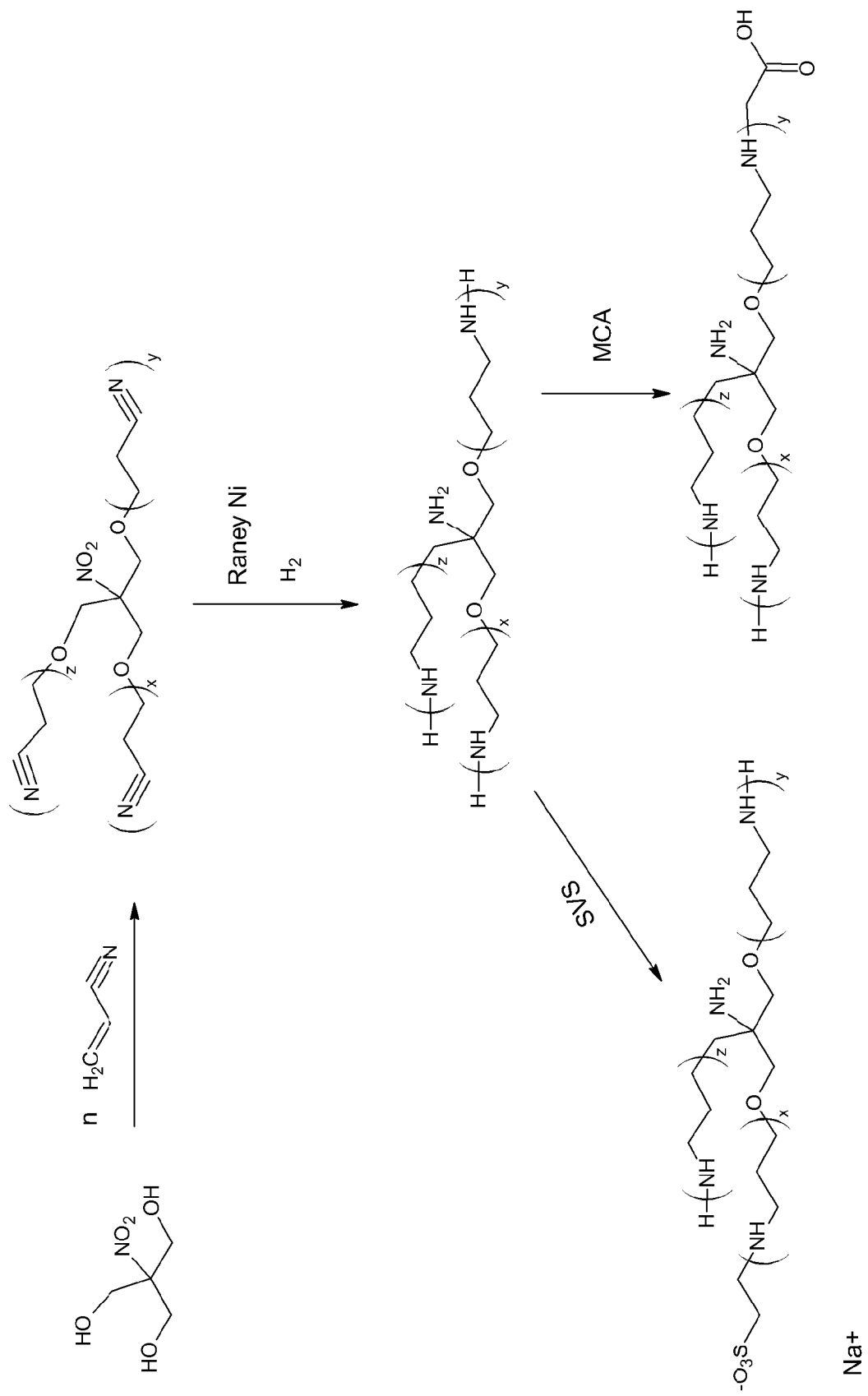
FIG. 6 shows the reaction of tris(hydroxymethyl)nitromethane with acrylonitrile and its derivatives where x, y, z, and n are all integers where x, y and z are chosen independently, such that x+y+z=n and n is greater than zero.

FIG. 6 shows the reaction of tris(hydroxymethyl)nitromethane with acrylonitrile and its derivatives where x, y, z, and n are all integers where x, y and z are chosen independently, such that x+y+z=n and n is greater than zero.

Figure 7:
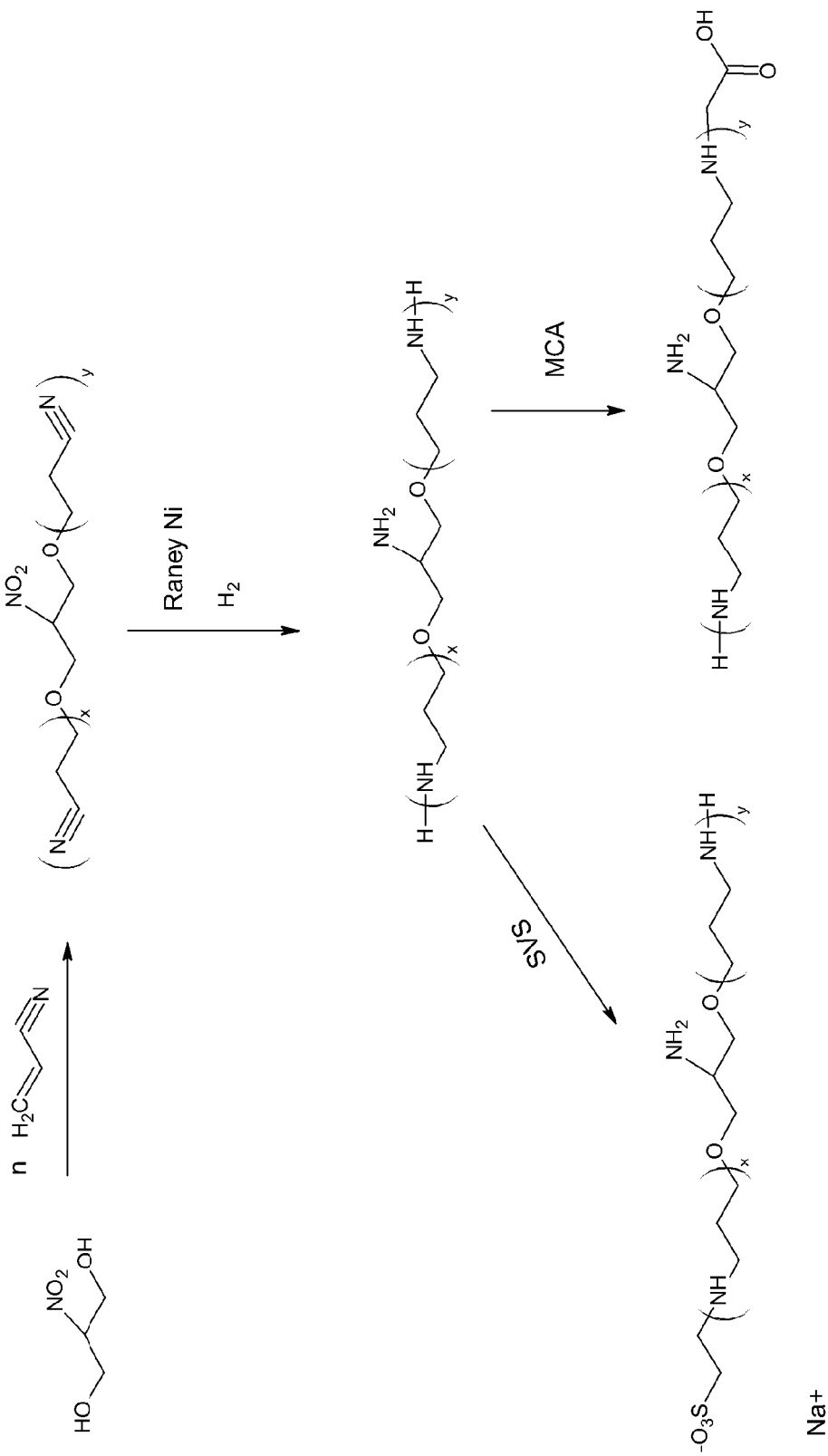
FIG. 7 shows the reaction of 2-nitro-1,3-propanediol with acrylonitrile and its derivatives where x, y, and n are all integers where x and y are chosen independently, such that x+y=n and n is greater than zero.

FIG. 7 shows the reaction of 2-nitro-1,3-propanediol with acrylonitrile and its derivatives where x, y, and n are all integers where x and y are chosen independently, such that x+y=n and n is greater than zero.

Figure 8:
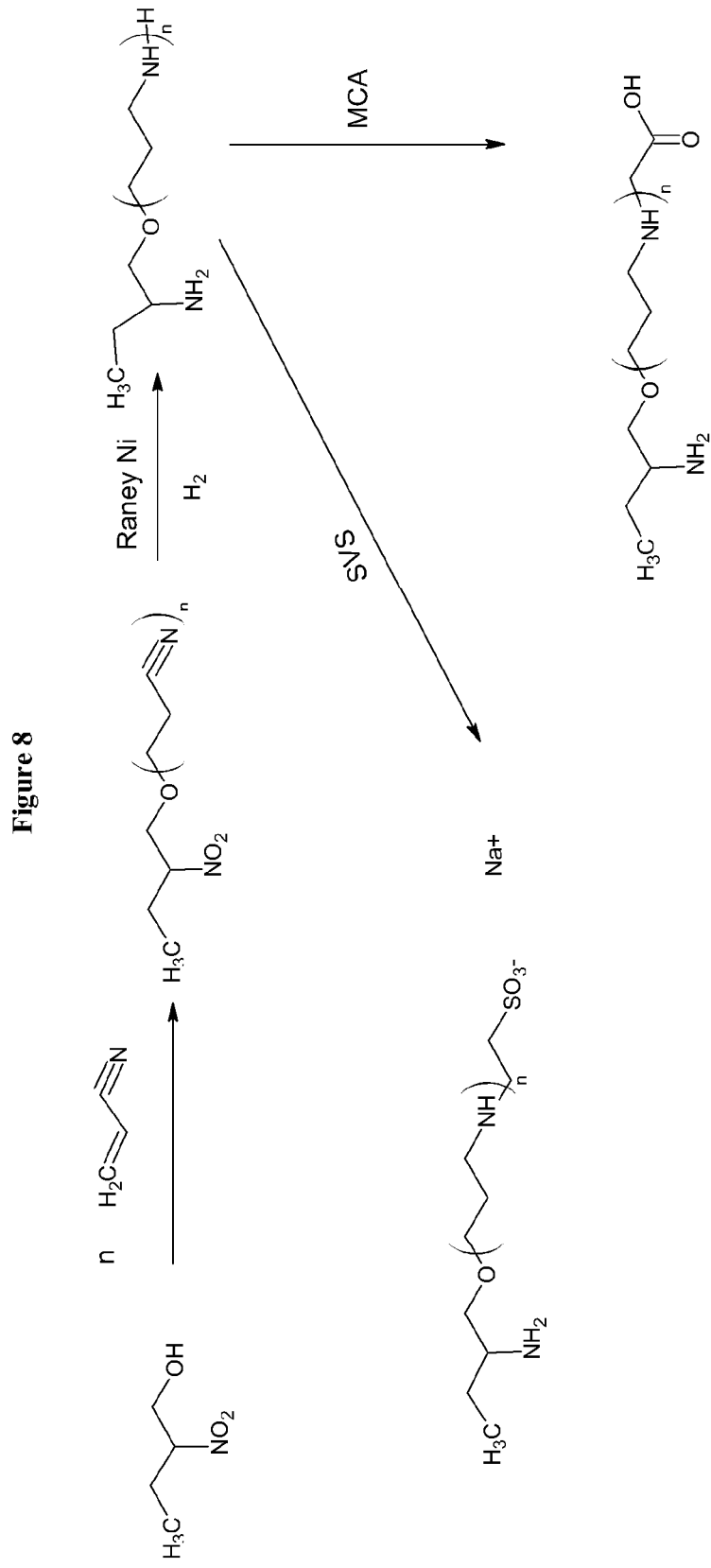
FIG. 8 shows the reaction of 2-nitro-1-butanol with acrylonitrile and its derivatives.

FIG. 8 shows the reaction of 2-nitro-1-butanol with acrylonitrile and its derivatives.

FIGS. 2 through 8 are subject to the same clarifications as FIG. 1 with regard to the cyanoethylation and the formation of a more linear or branched structure as well as the addition of SVS or MCA in molar equivalents of primary amine groups or less than molar equivalents of primary amine groups present.

Figure 9:
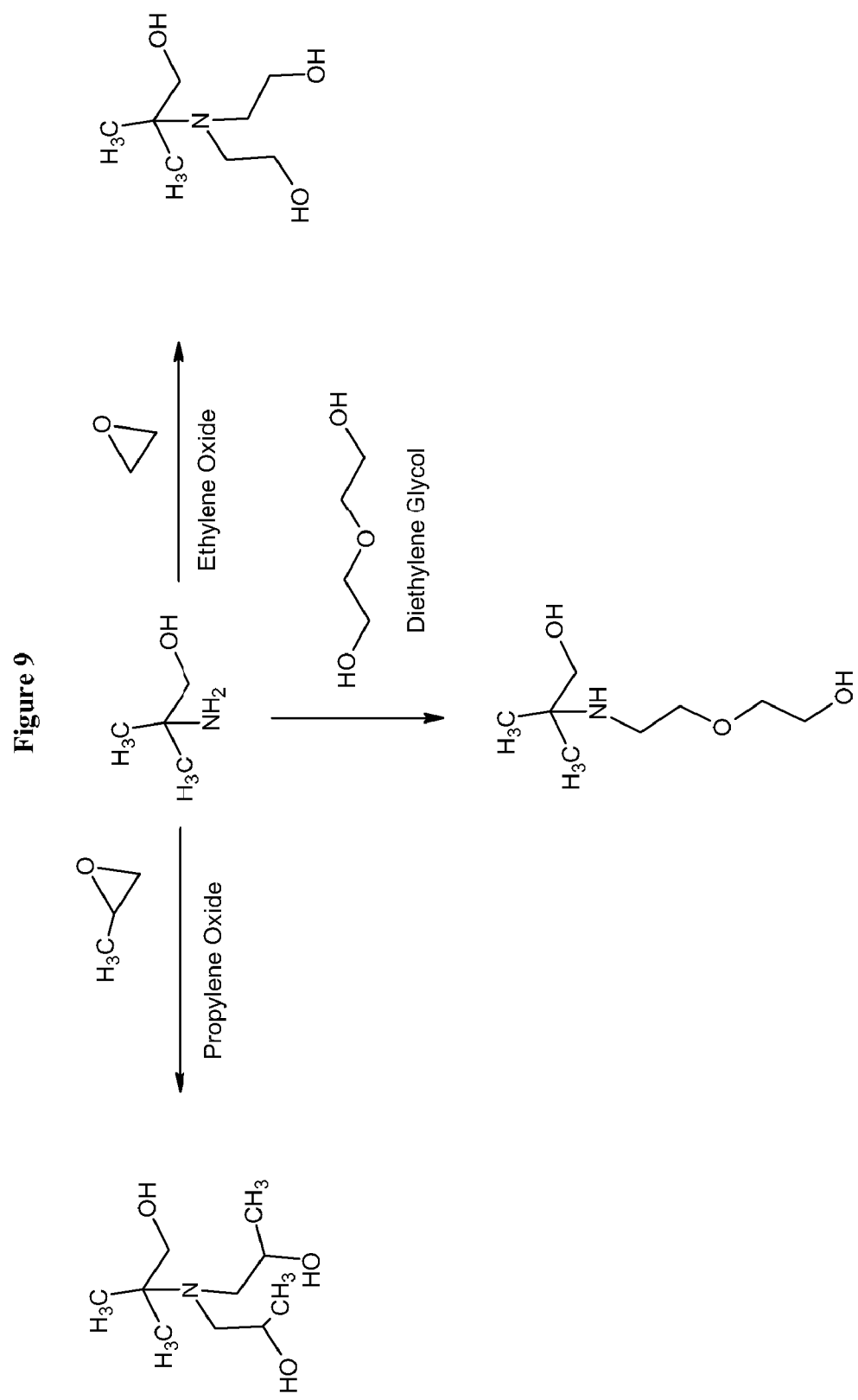
FIG. 9 shows

The buffers described thus far may also be ethoxylated, propoxylated, or butoxylated to modify their properties. Ethoxylation will tend to impart surfactancy to the resulting product. Propoxylation will add surfactancy, but also reduce the water solubility. This is useful in emulsion breaking and reverse emulsion breaking, this will also find utility in breaking up and dissolving biofilms. This is also desired in oil-field applications. Butoxylation will similarly shift the HLB to the hydrophobic. Combinations of ethoxylation, propoxylation, and butoxylation can be tailored to specific emulsion and reverse emulsion forming and breaking requirements. FIG. 9 shows alkoxylation of aminomethylpropanol. The direct 2 mole ethoxylation of 2-amino-2-methyl-1-propanol with 2 moles of ethylene oxide, as shown in FIG. 9 produces an excellent biological buffer with less chelation than 2-amino-2-methyl-1-propanol. The reaction of 2-amino-2-methyl-1-propanol with propylene oxide or butylene oxide yields a similarly less chelating product, as does the reaction with diethylene glycol. The reaction product of 2-amino-2-methyl-1-propanol with 1 mole of diethylene glycol as shown in FIG. 9 produces an ideal amine for gas scrubbing of $H_2S$. This product is particularly useful because it does not bind to carbon dioxide and carbon monoxide in any appreciable amount. Thus making it ideal for tail gas scrubbing and maximizing the capacity of sulfur plants in refineries. Similar performance is seen with the reaction of the following amines 2-amino-1-butanol, 2-amino-2-methyl-1,3-propanediol, 2-amino-2-ethyl-1,3-propanediol, tris(hydroxylmethyl)aminomethane, and 2-amino-1,3-propanediol.

Figure 10:
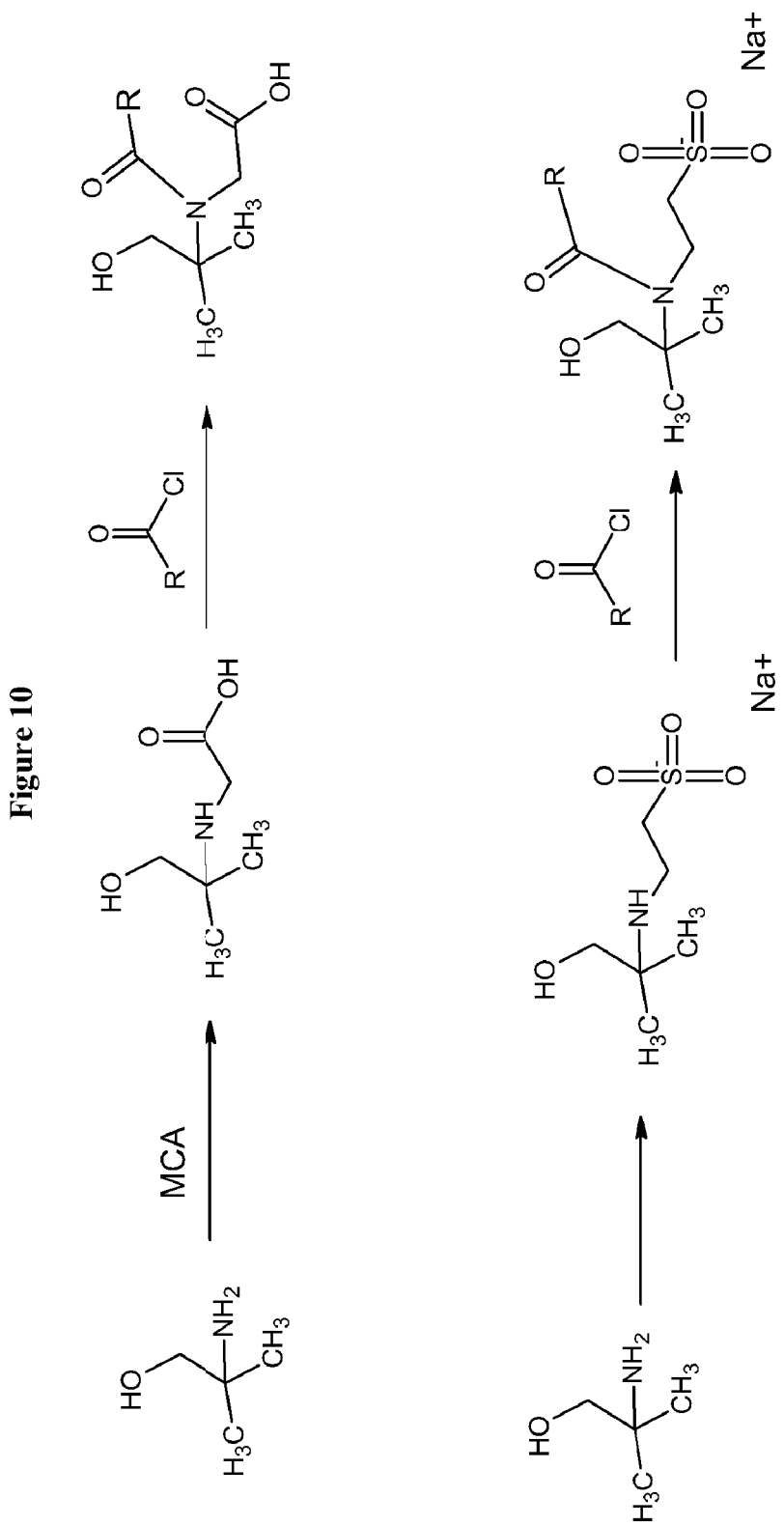
FIG. 10 shows the synthesis of a very mild, high foaming, surfactant derived from MCA and the synthesis of a very mild, high foaming, surfactant derived from SVS.

The buffers described herein also make excellent starting materials for surfactants. FIG. 10 shows the synthesis of two very mild, high foaming, surfactants that are well suited for personal care applications were irritation is problematic, such as baby shampoo and face cleansers. Similar results are seen when 2-amino-1-butanol, 2-amino-2-methyl-1,3-propanediol, 2-amino-2-ethyl-1,3-propanediol, tris(hydroxylmethyl)aminomethane, and 2-amino-1,3-propanediol are used as the starting material in place of 2-amino-2-methyl-1-propanol.

Figure 11:
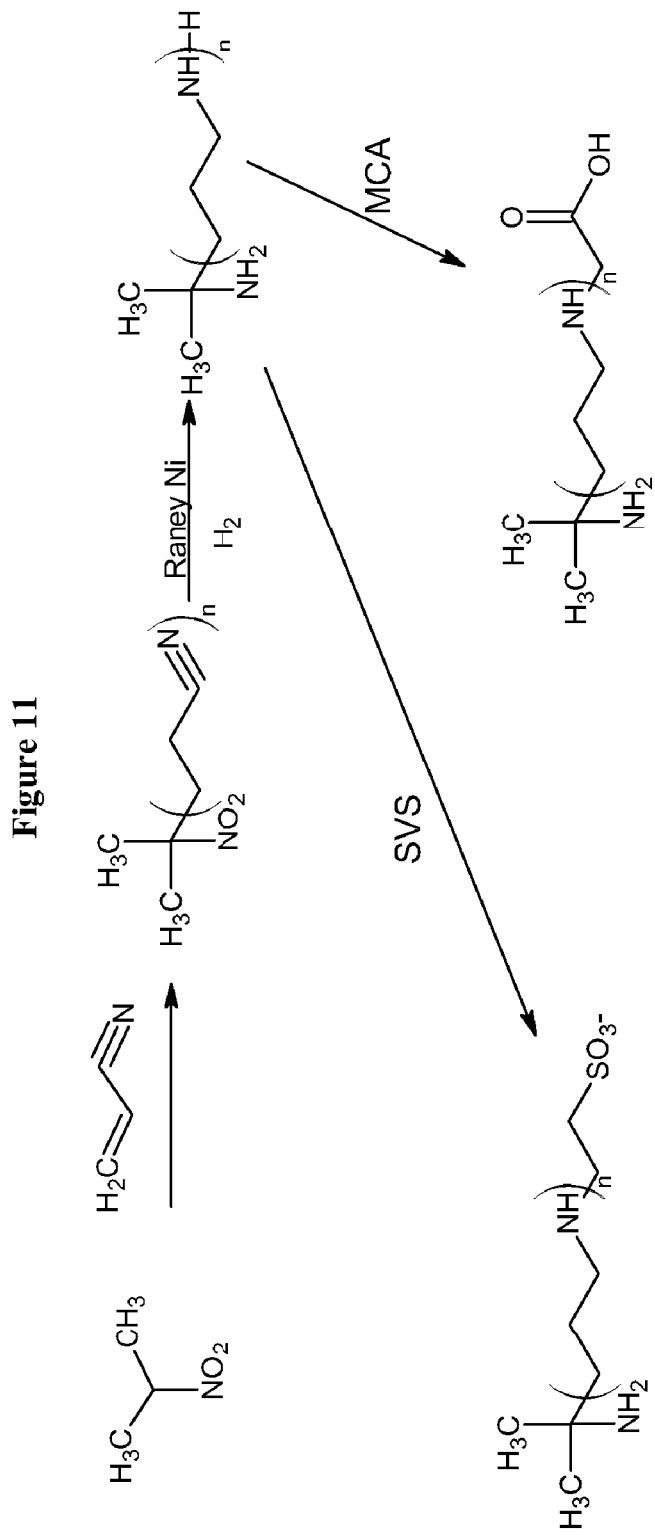
FIG. 11 shows the synthesis of a series of buffers with 2-nitropropane as the starting material.
Figure 12:
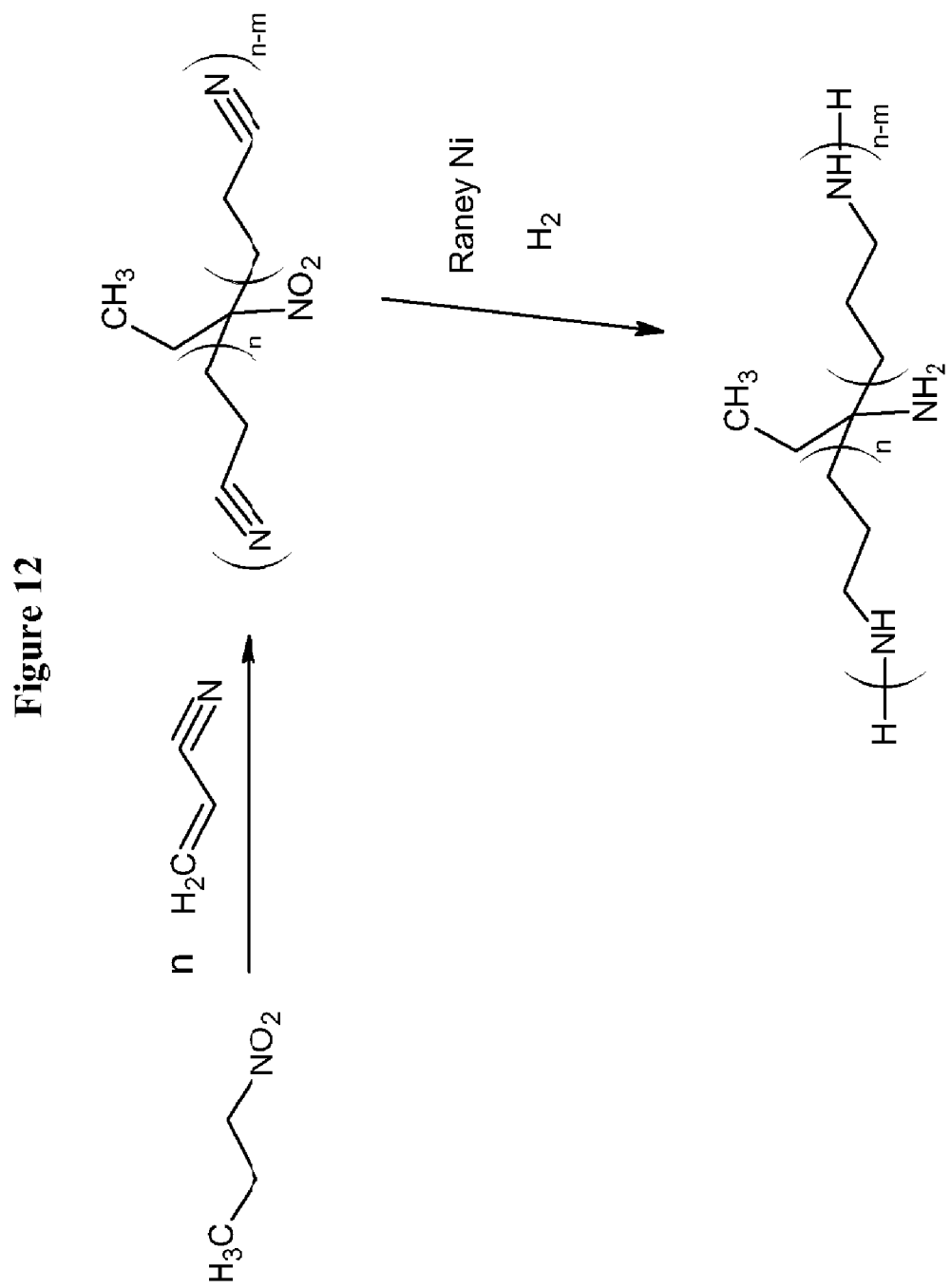
FIG. 12 shows

Polyamines with good properties for use in biological fermentations, purifications, storage and general handling can also be produced through the reaction of nitroalkanes and acrylonitrile, followed by reduction. Additional derivatization with SVS or MCA will result in zwitterionic buffers with a very large buffering range and capacity. FIG. 11 shows the synthesis of a series of buffers with 2-nitropropane as the starting material. FIG. 12 shows the synthesis of a series of buffers with 1-nitropropane as a starting material where n and m are integers where m+n is greater than zero and n is greater than or equal to m. Branching can be imparted on the buffers described in FIGS. 11 through 14 for the polyamines that have greater than 3 amine groups by reducing the resulting nitrile or polynitrile to the polyamine and then reacting with more acrylonitrile and then reducing the resulting nitrile groups to amine groups. This can be done repeatedly. As in FIG. 1, conditions can be chosen such that a more branched product results. A more linear product is produced by simply adding all the acrylonitrile in one step, and then reducing the resulting polynitrile to the polyamine. For FIGS. 12 through 14, the zwitterionic products can be made by adding MCA or SVS as shown in FIGS. 2 through 8.

Figure 13:
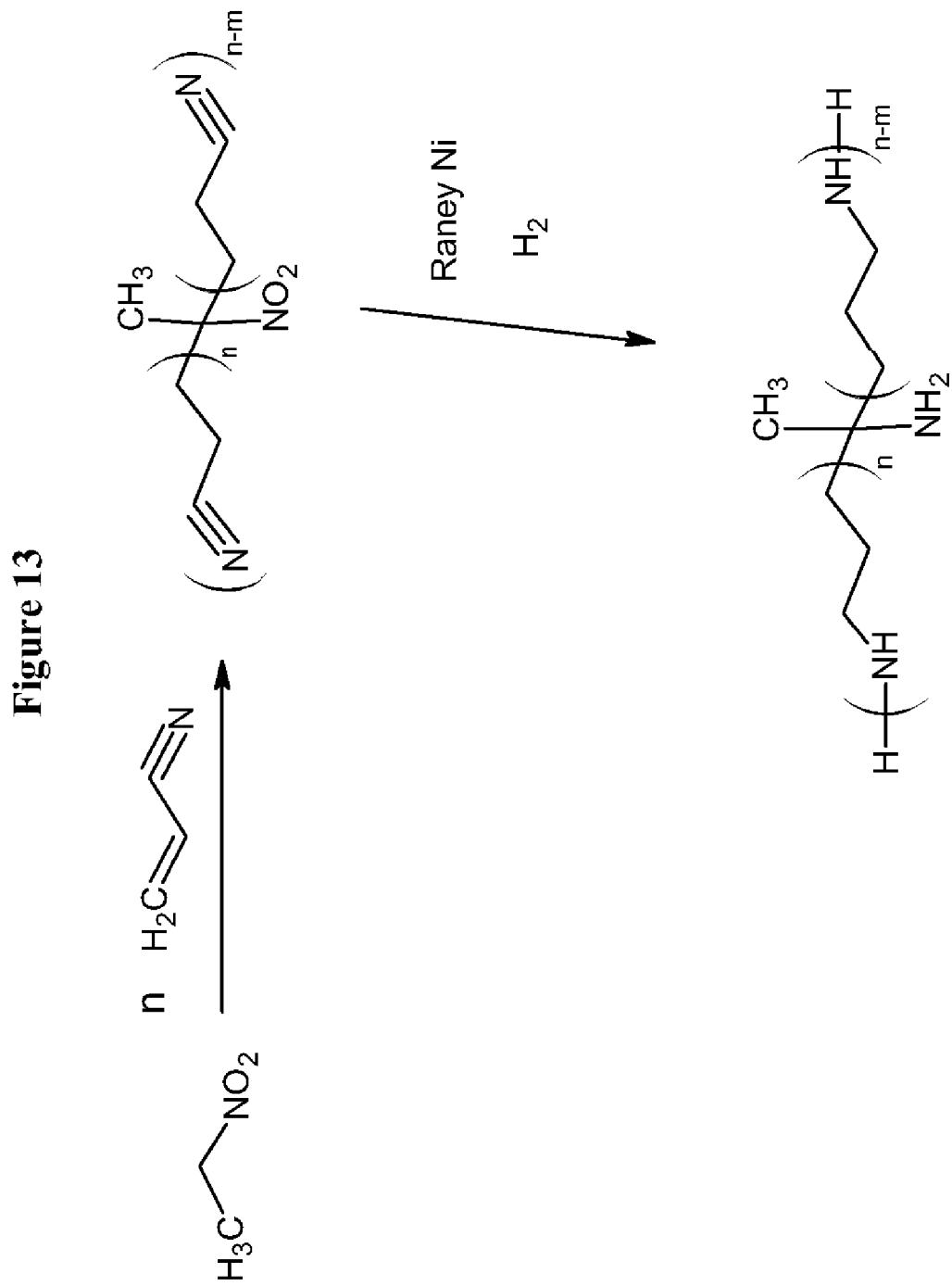
FIG. 13 shows the synthesis of a series of buffers with nitroethane as a starting material where n and m are integers where m+n is greater than zero and n is greater than or equal to m.
Figure 14:
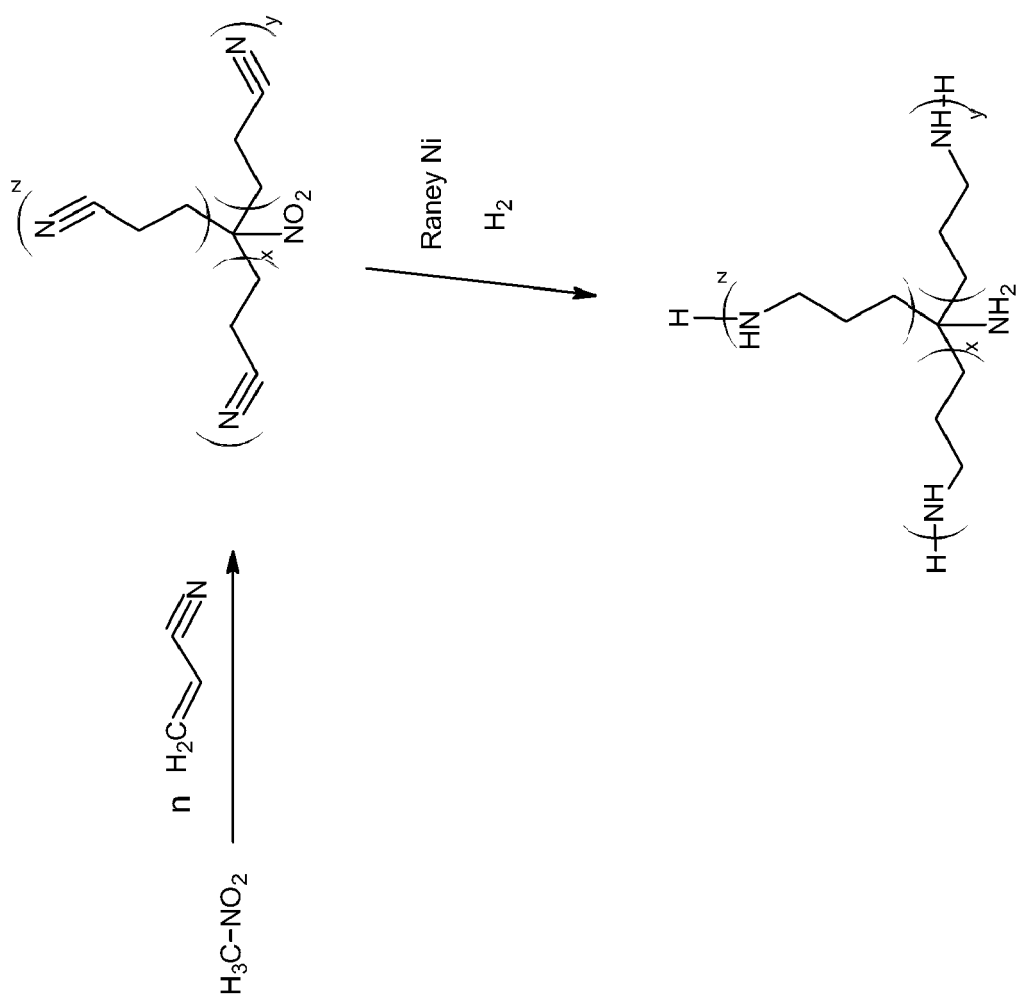
FIG. 14 shows the synthesis of a series of buffers with nitromethane as a starting material where x, y, z and n are integers and x+y+z=n and n is greater than zero.

FIG. 13 shows the synthesis of a series of buffers with nitroethane as a starting material where n and m are integers where m+n is greater than zero and n is greater than or equal to m. FIG. 14 shows the synthesis of a series of buffers with nitromethane as a starting material where x, y, z and n are integers and x+y+z=n and n is greater than zero.

Several descriptions and illustrations have been presented to enhance understanding of the present invention. Numerous changes and variations are possible without departing from the spirit of the invention. Each of these changes and variations are within the scope of the present invention.

Figure 15:
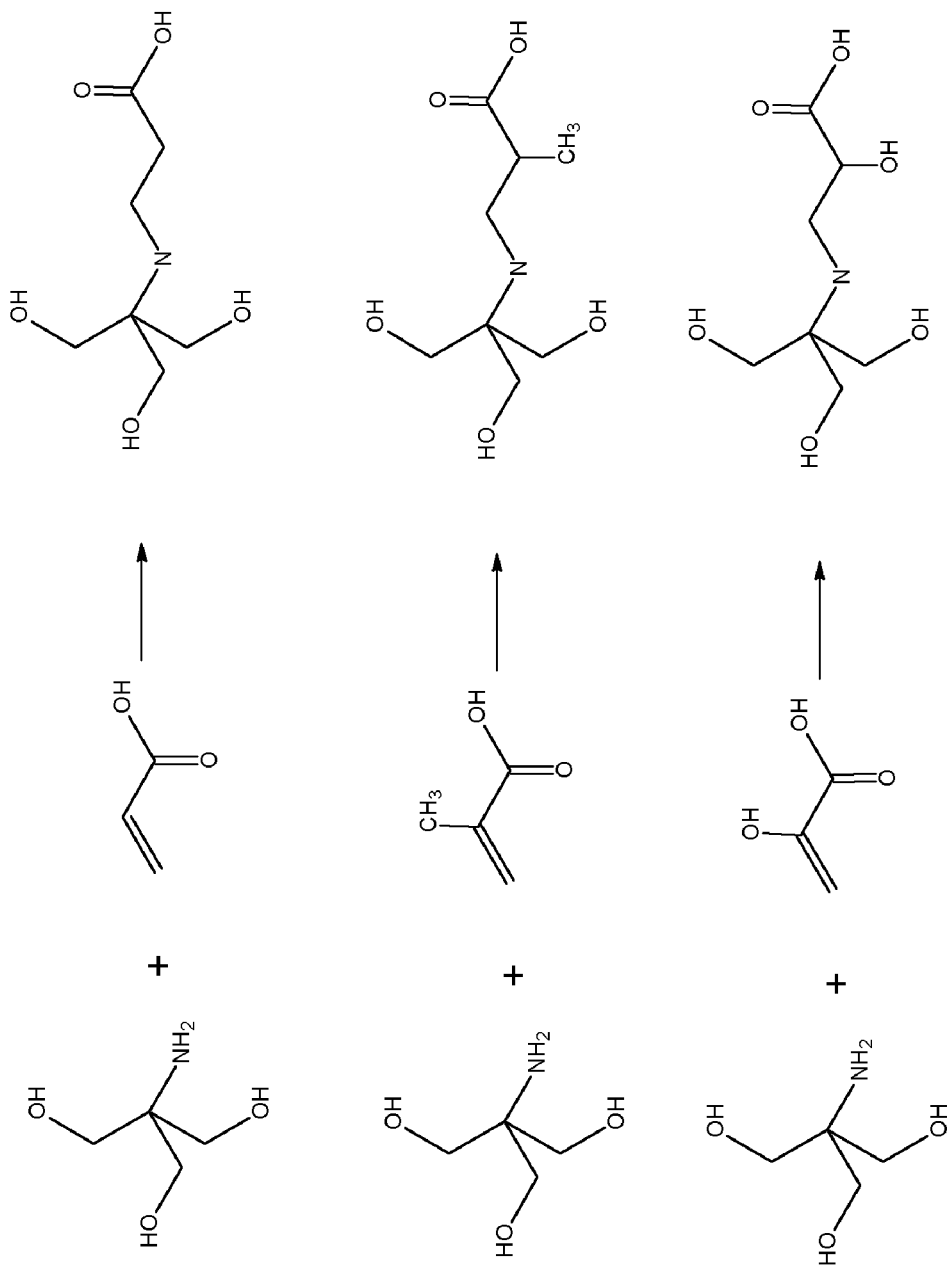
FIG. 15 shows the synthesis of a series of zwitterionic buffers based on acrylic acids.

Another embodiment of the present invention is the synthesis of zwitterionic buffers with vinyl acids. FIG. 15 shows the synthesis of a family of zwitterionic buffers based on members of the acrylic acid family. However, other vinyl acids may be used. Vinyl acids such as acrylic, 3-butenoic acid, 4-pentenoic acid, and other carboxylic acids with a double bond at the terminus. Carboxylic acids with a triple bond at the terminus also can be utilized, similarly, an acid where the multiple bond is not at the terminus, such as hex-4-enoic acid, can also be utilized. However, due to the reduced commercial availability of such compounds, the preferred embodiment is the vinyl acid with a double bond at the terminus. One very large benefit of utilizing vinyl acids to make zwitterionic buffers is that the product does not need to be ion exchanged to produce a non-ionized form. In the market, both ionized, or sometimes called salted, and non-ionized forms sometimes called free acid or free base, are required. In situations where ionic strength must be very closely controlled, the non-ionized forms are more popular. For cases where increased water solubility and ease of solution are desired, the salted forms are preferred. The present invention covers both the ionized and non-ionized forms of the buffers disclosed herein.

Figure 16:
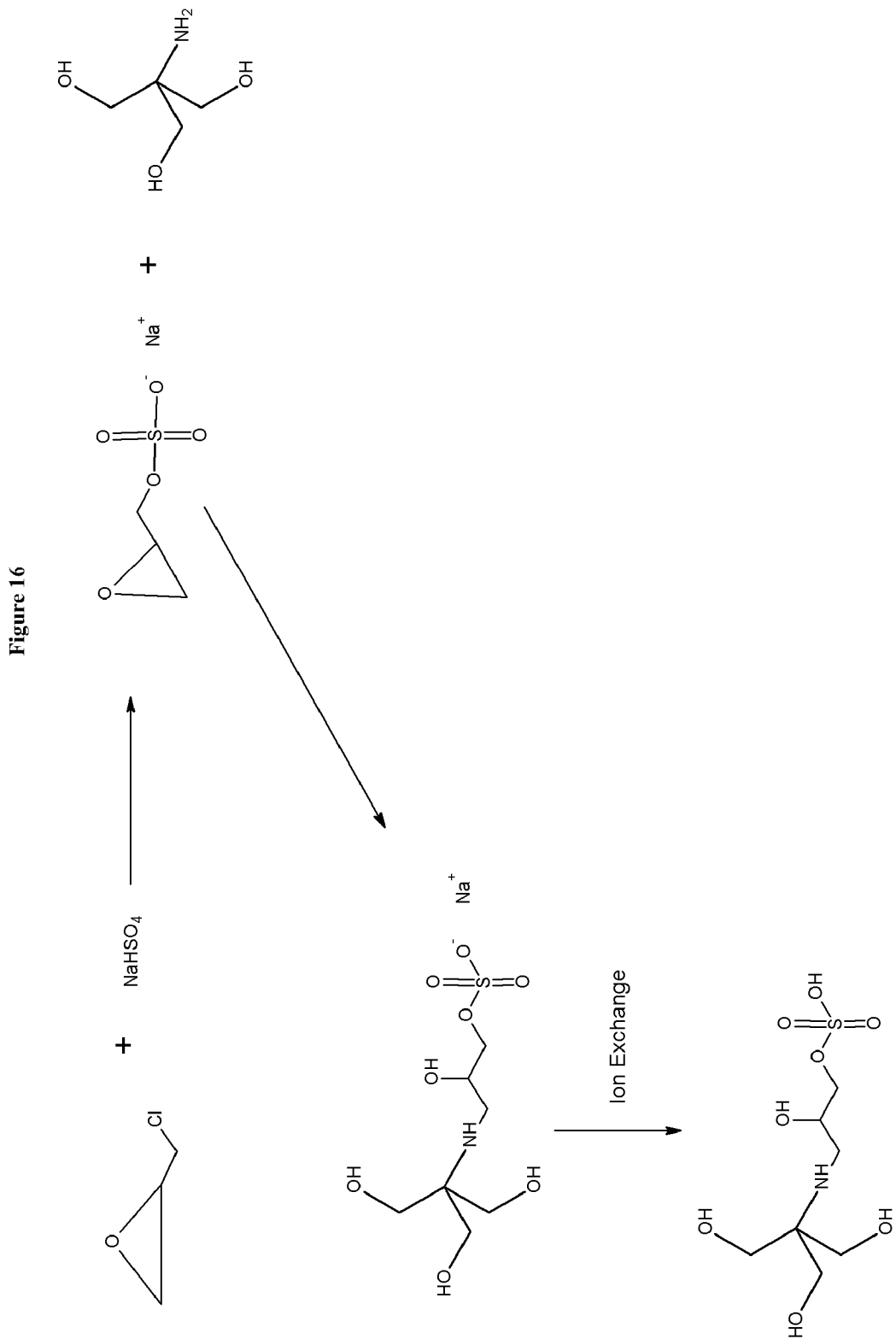
FIG. 16 shows the synthesis of a zwitterionic sulfonate based on tromethamine.
Figure 17:
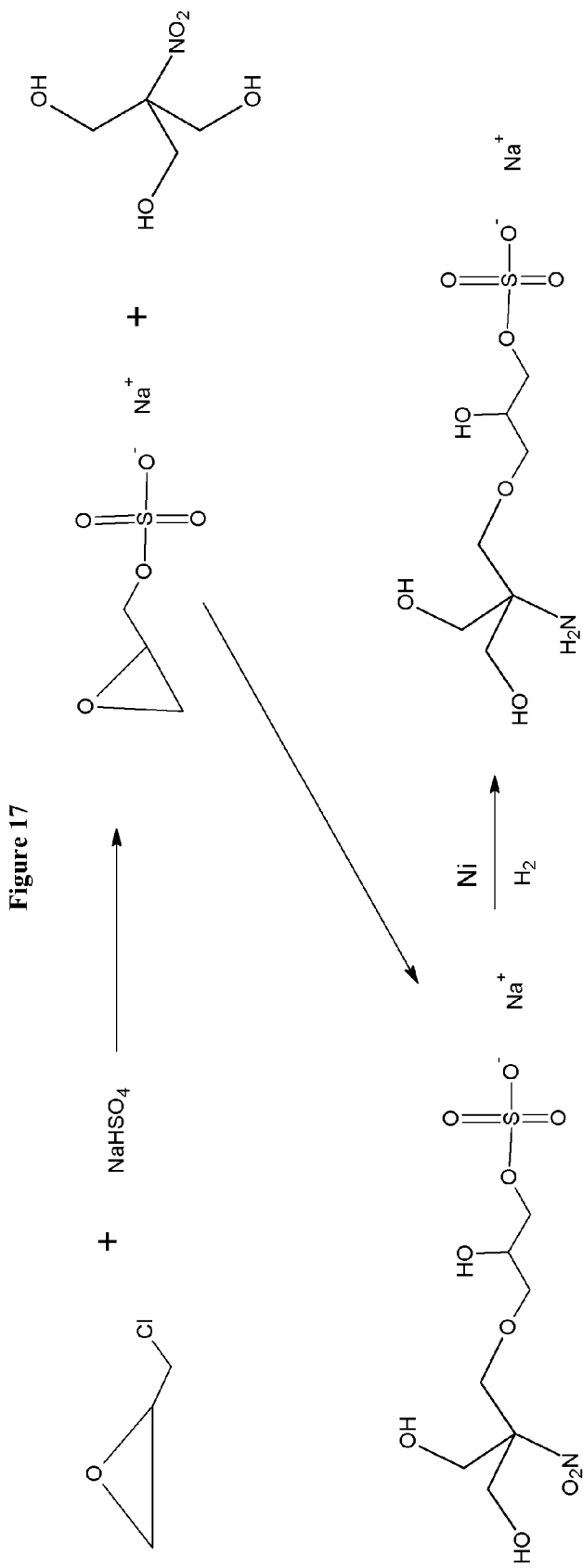
FIG. 17 shows the synthesis of a zwitterionic sulfonate based on aminomethylpropanol.
Figure 18:
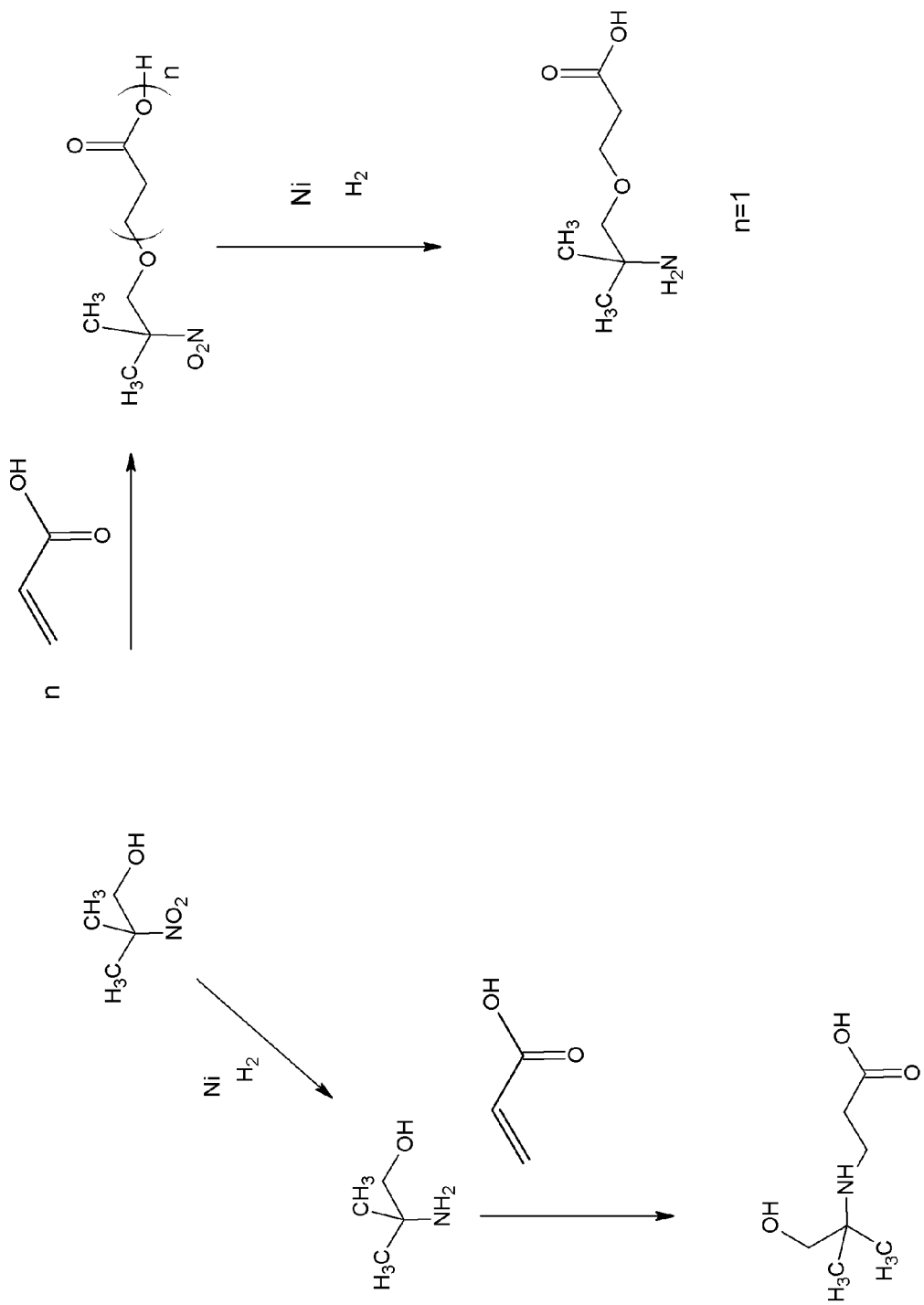
FIGS. 18-25 show the synthesis of families of zwitterionic buffers from nitroalcohols.
Figure 19:
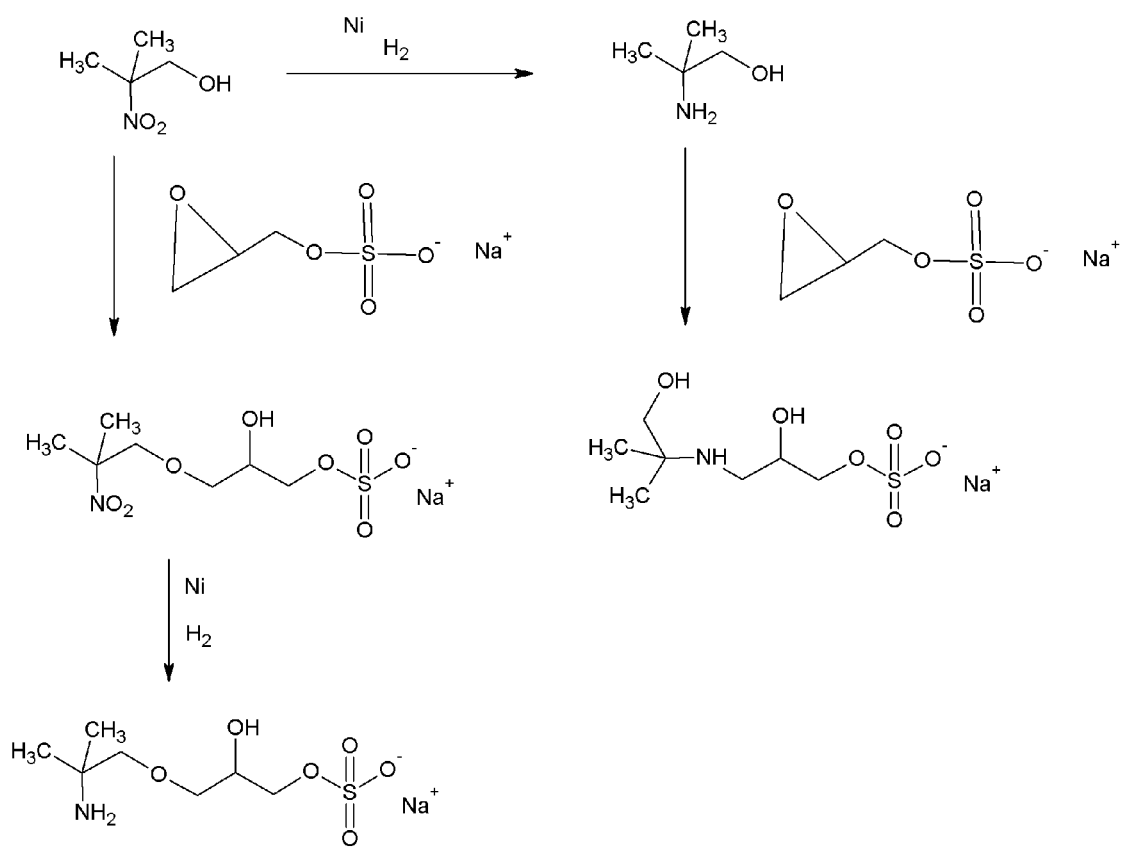
Figure 20:
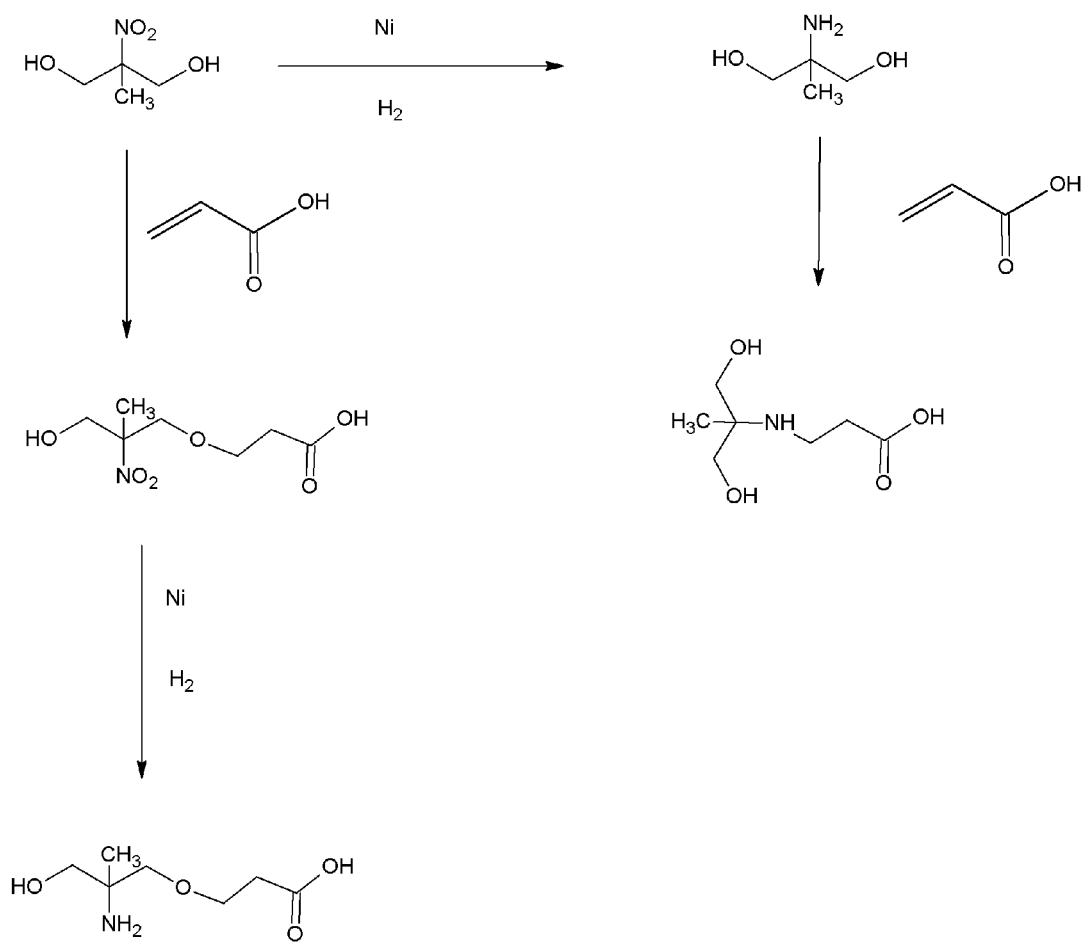
Figure 21:
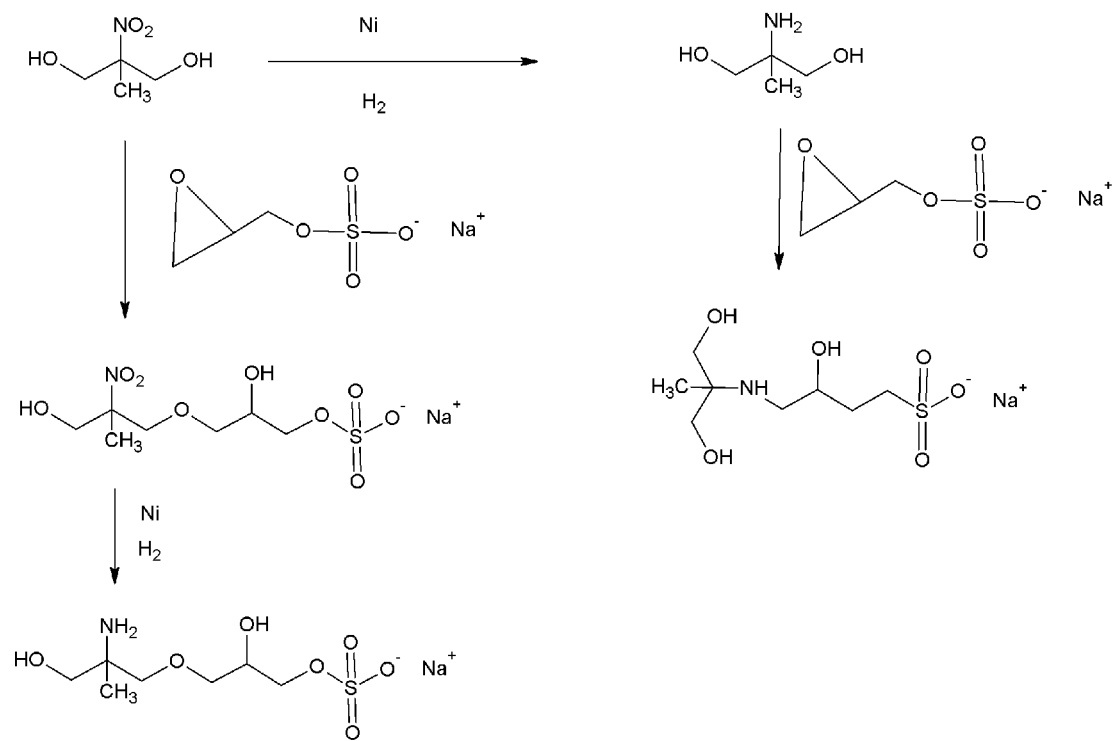
Figure 22:
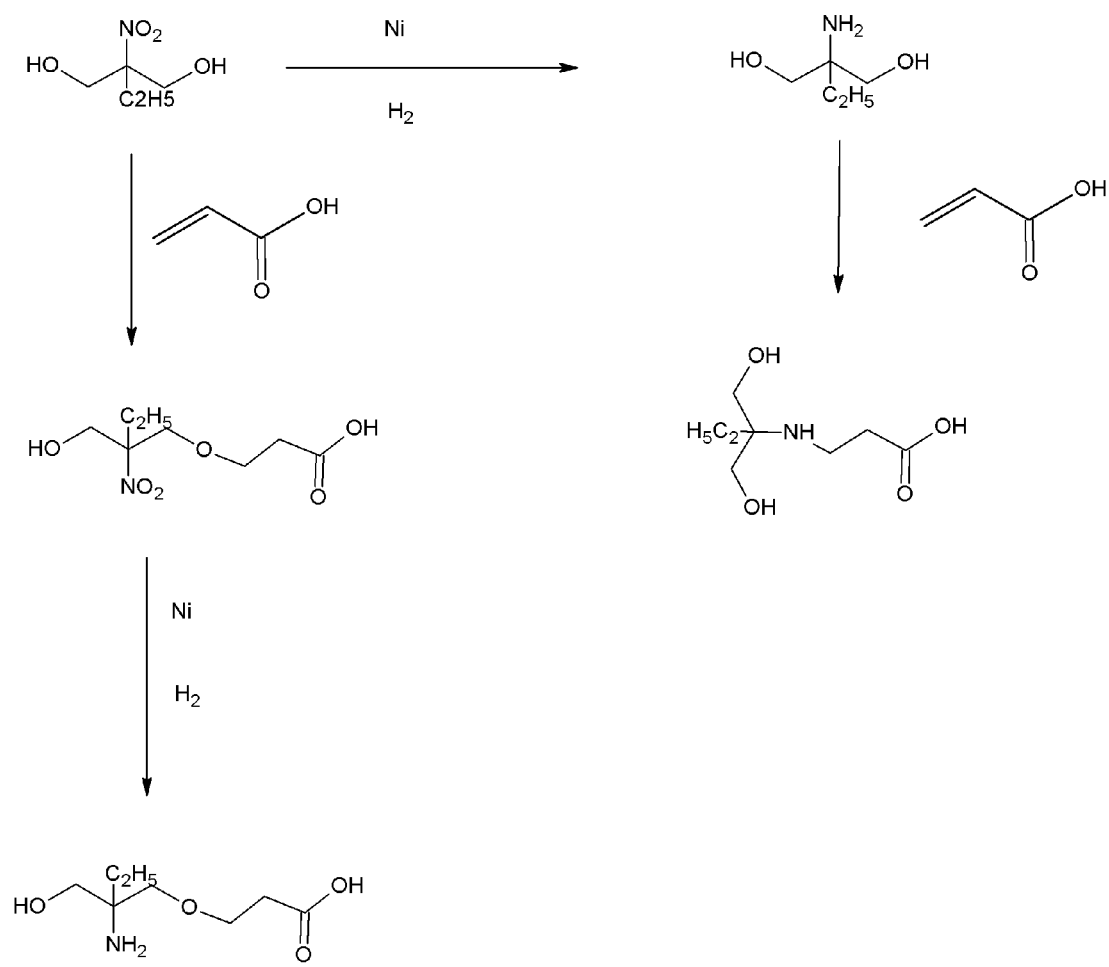
Figure 23:
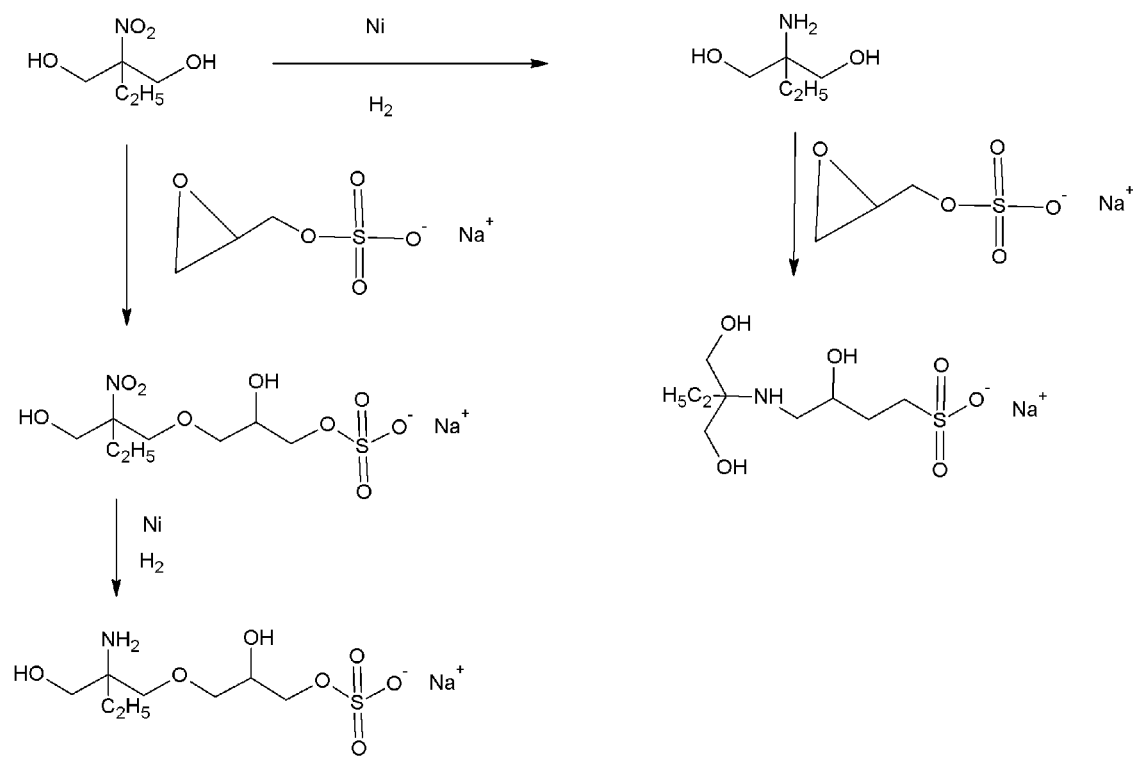
Figure 24:
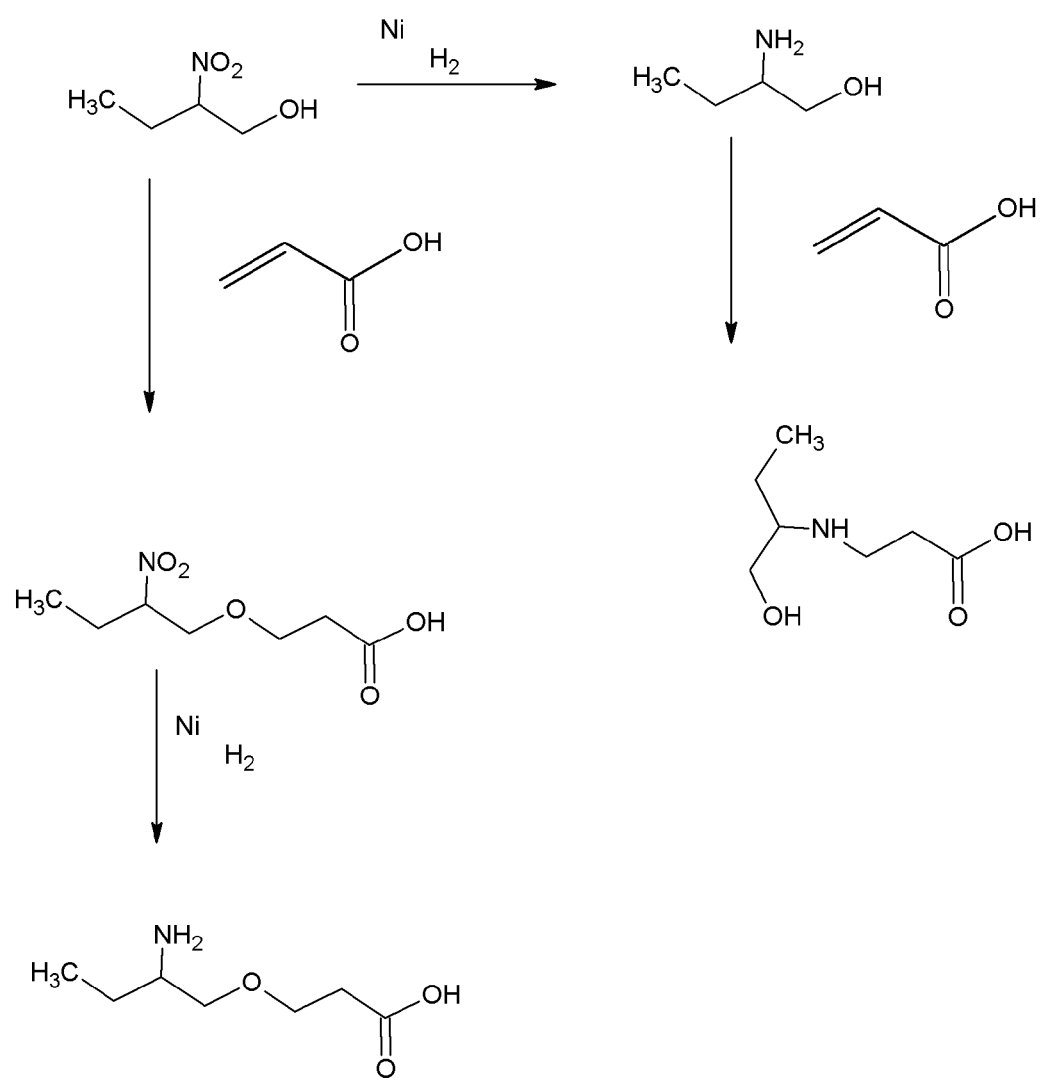
Figure 25:
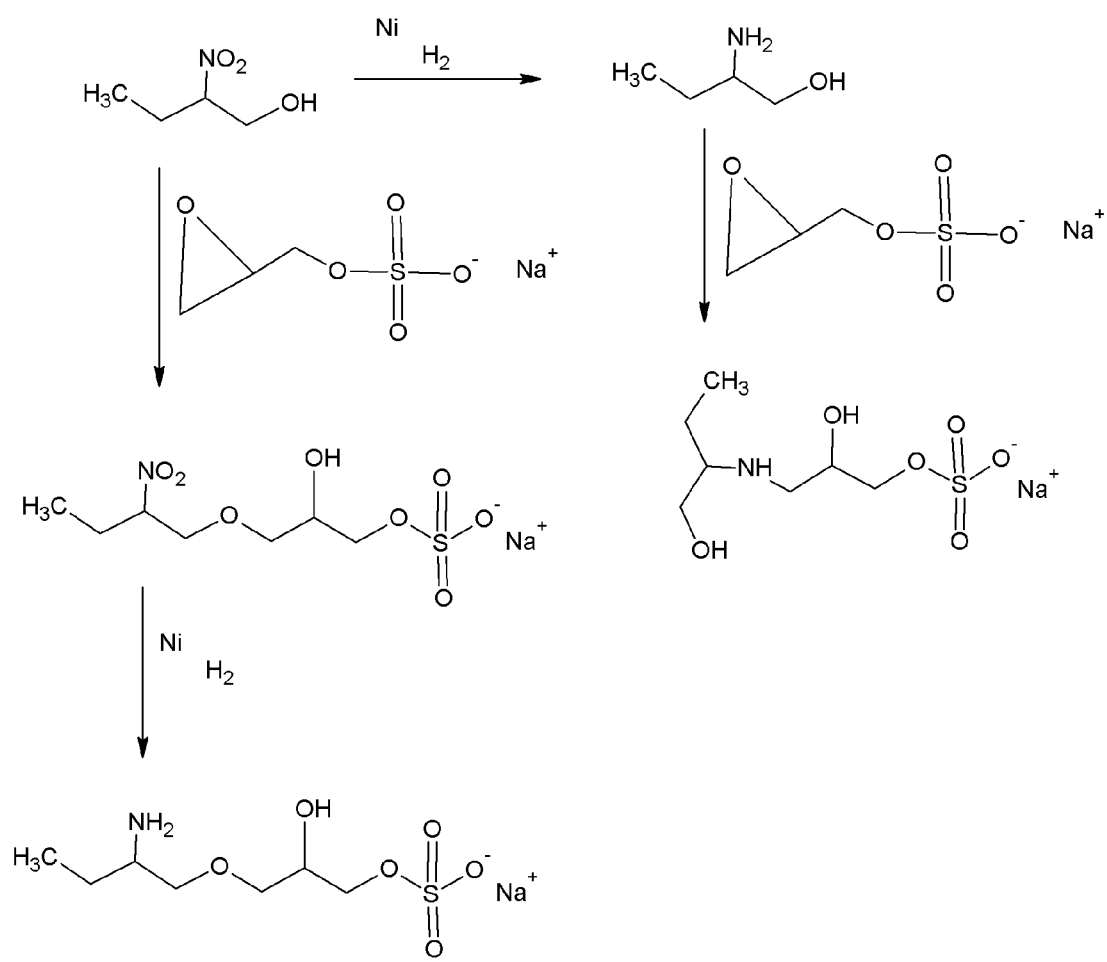

Another embodiment of the present invention is the sulfonate zwitterionic buffers derived from the reaction of an amine with an epichlorohydrin and sodium bisulfate condensate as described in FIG. 16. Other sulfate salts can be utilized to arrive at the desired molecular structure and is included in the present invention. FIGS. 17 through 25 teach the flexibility of the present invention to synthesize a series of a amine sulfonate or amino acid zwitterionic buffers from nitroalcohols or alkanolamines to produce zwitterionic buffers that have primary amino functionality or secondary amino functionality. In cases where there are more than one reactive group, amine, alcohol, or a combination, multiple sulfonate groups or acid groups can be reacted by adding more than one equivalent of the vinyl acid or the oxirane containing sulfonate.

Figure 26:
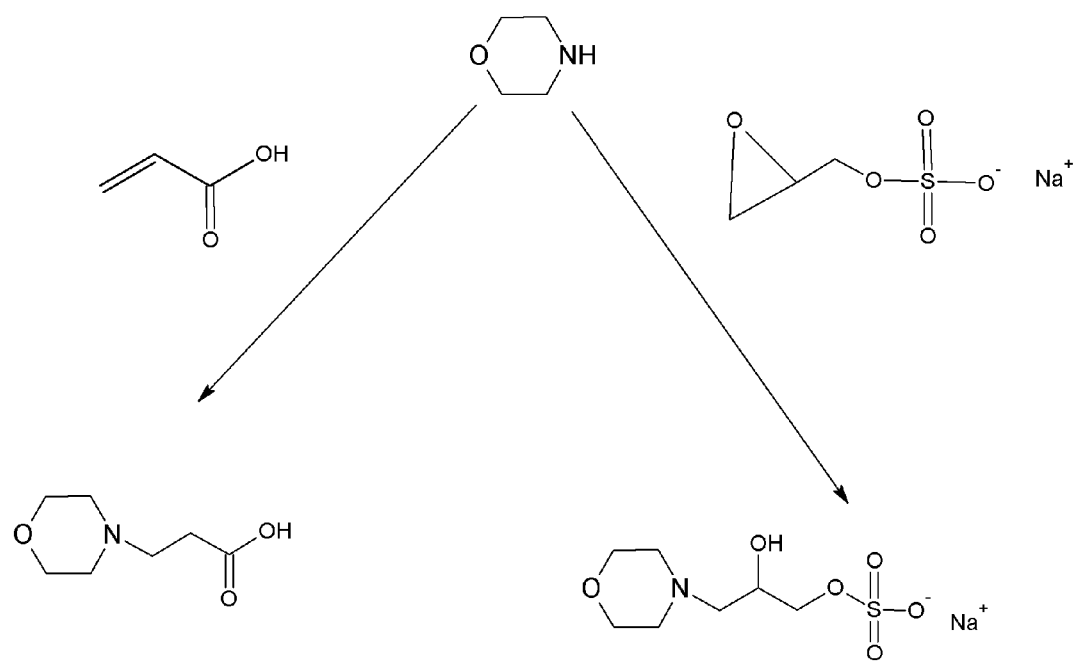
FIG. 26 shows the synthesis of zwitterionic buffers from morpholine.
Figure 27:
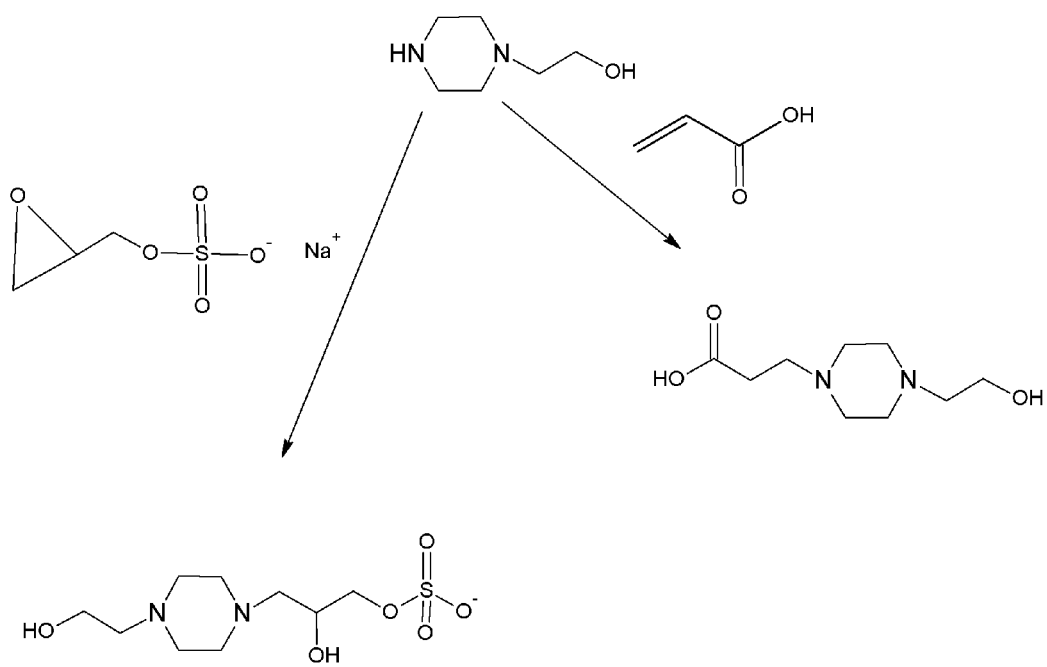
FIG. 27 shows the synthesis of zwitterionic buffers from hydroxyethyl piperazine.
Figure 28:
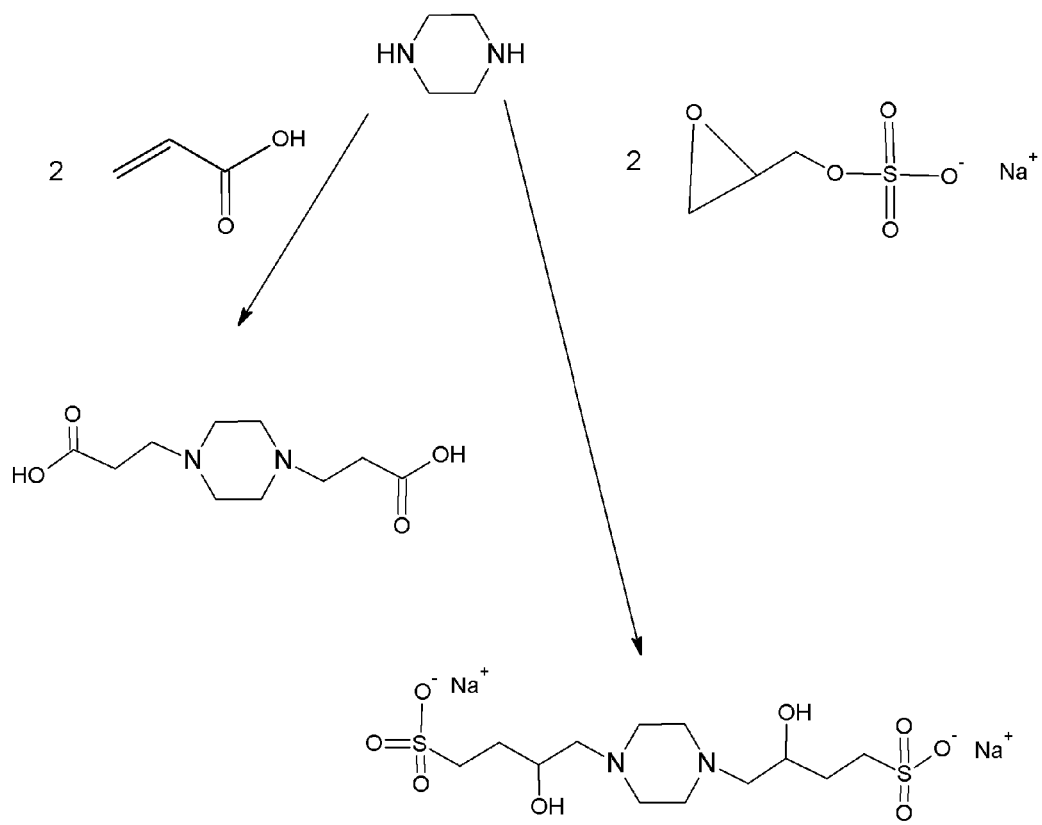
FIG. 28 shows the synthesis of zwitterionic buffers from piperazine.
Figure 29:
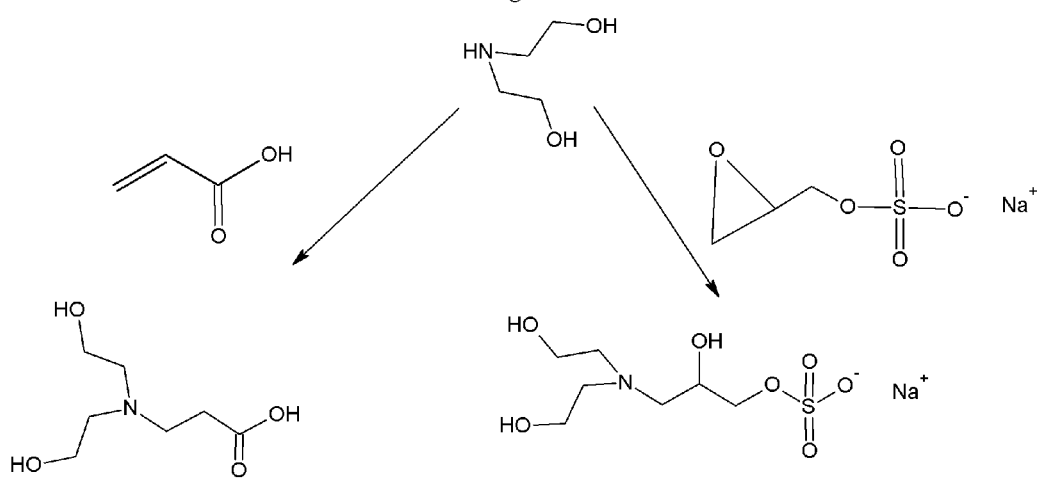
FIG. 29 shows the synthesis of zwitterionic buffers from ethyleneamines.
Figure 29:
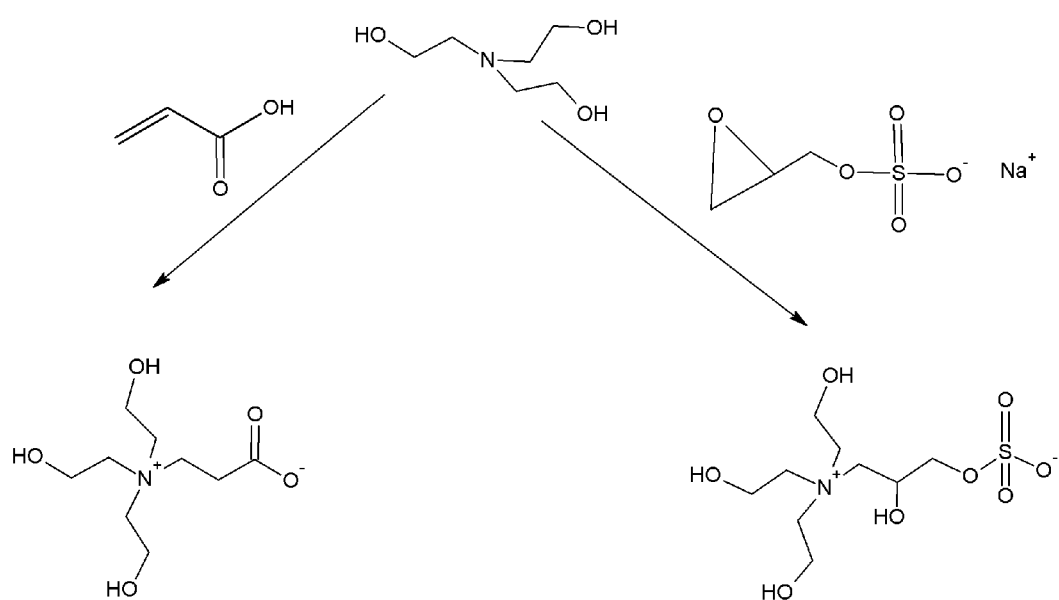

Another embodiment of the current invention is to make zwitterionic buffers with cycloamines as the starting material. The cycloamines result in a tertiary amino group that is less chelating and interferes less in biological functions. FIG. 26 shows the reaction of morpholine with a vinyl acid and morpholine with the oxirane sulfonate. FIG. 27 teaches similar products, but utilizing hydroxyethyl piperazine. FIG. 28 teaches the use of diamines as starting materials by using piperazine as the starting material. This is a good example of a synthesis of polyzwittterionic buffers as discussed earlier. FIG. 29 teaches the use of ethylene amines to make zwitterionic buffers through reaction with vinyl acids or oxirane sulfonates. Similar compounds can be made by using ethylene amines, such as monoethanolamine and the higher homologs, such as diethylenetriamine and is part of the invention disclosed herein.

Figure 30:
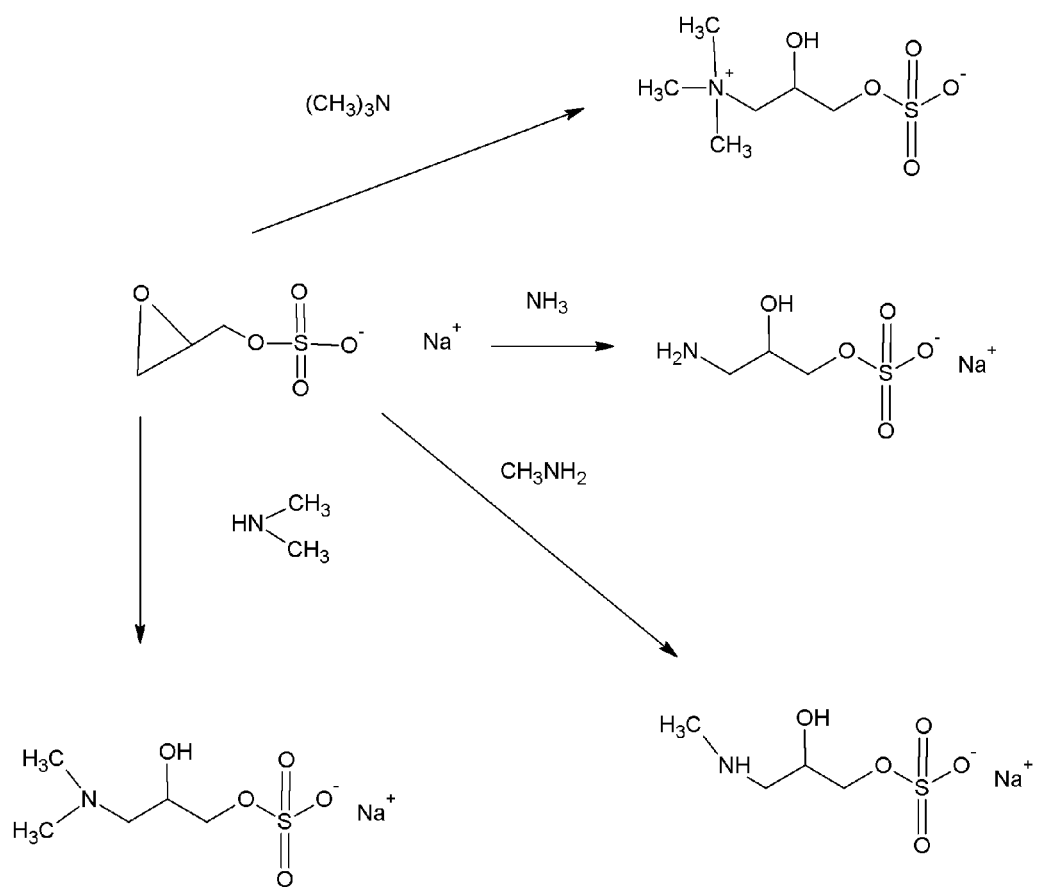
FIG. 30 shows the synthesis of a zwitterionic buffer with primary, secondary, tertiary, or quaternary amine functionality.

Another embodiment of the current invention is the synthesis of zwitterionic amines that have primary, secondary, tertiary, and quaternary amine functionality. FIG. 30 teaches this via oxirane sulfonate and amines. It is obvious to one in the art that any primary, secondary, or tertiary amine can be used in place of the methyamines in FIG. 30. While not shown in the figure, the resulting amines can be reacted further with vinyl acids, monochloroacetic acid, sodium vinyl sulfonate, or an oxirane sulfonate to further add acidic character to the zwitterionic buffer.

Figure 31:
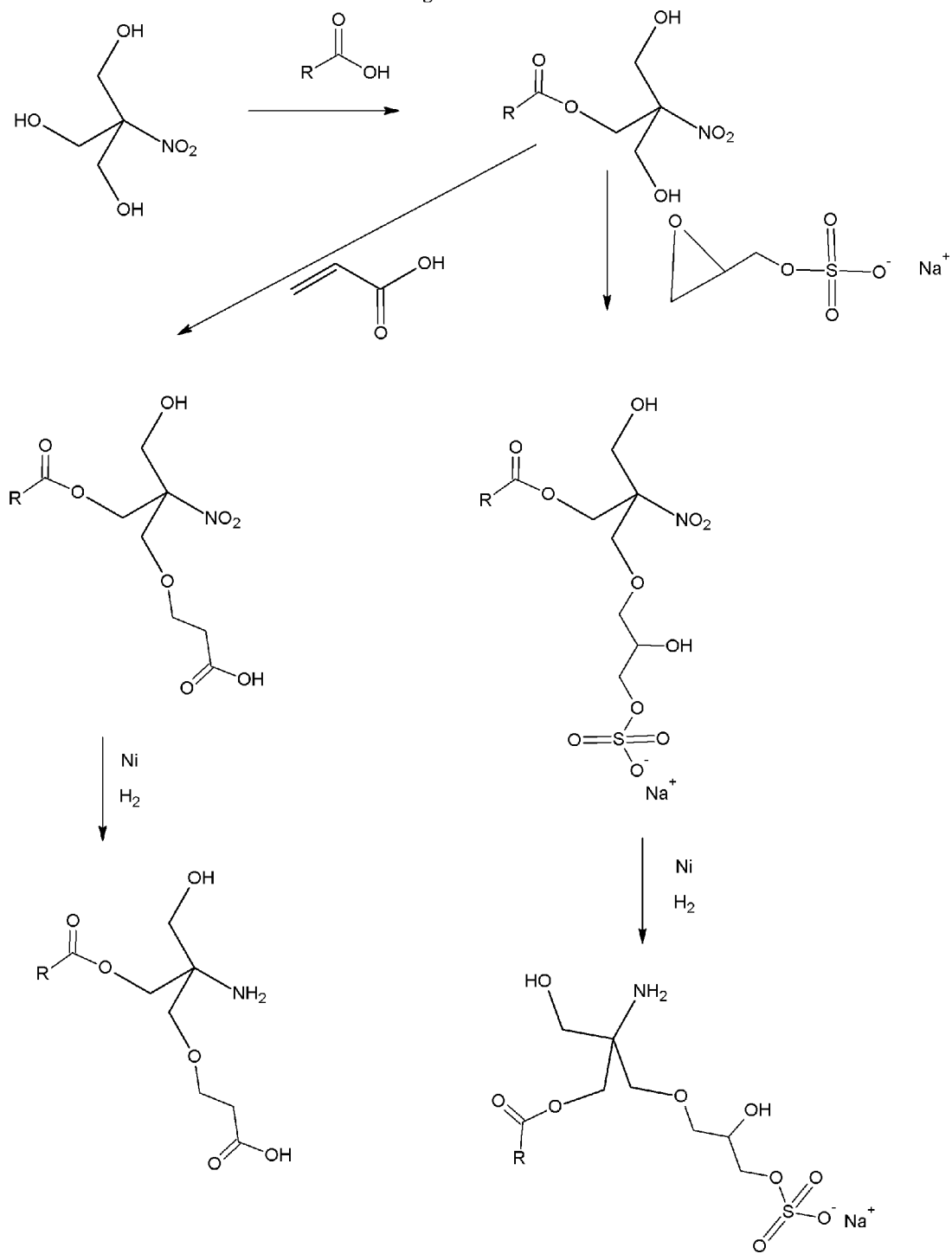
FIGS. 31-33 show the synthesis of mild zwitterionic surfactants from nitroalcohols.
Figure 32:
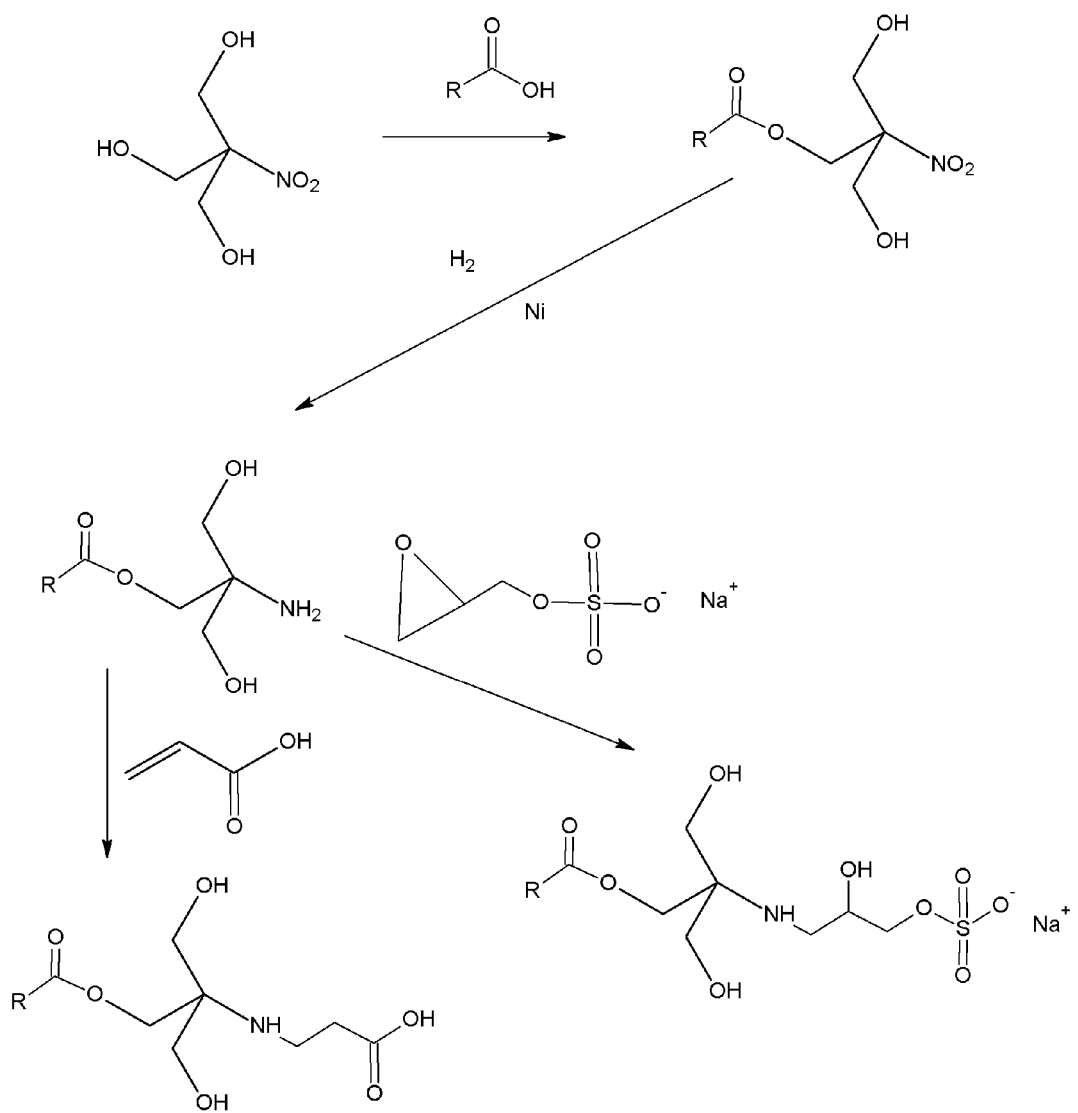
Figure 33:
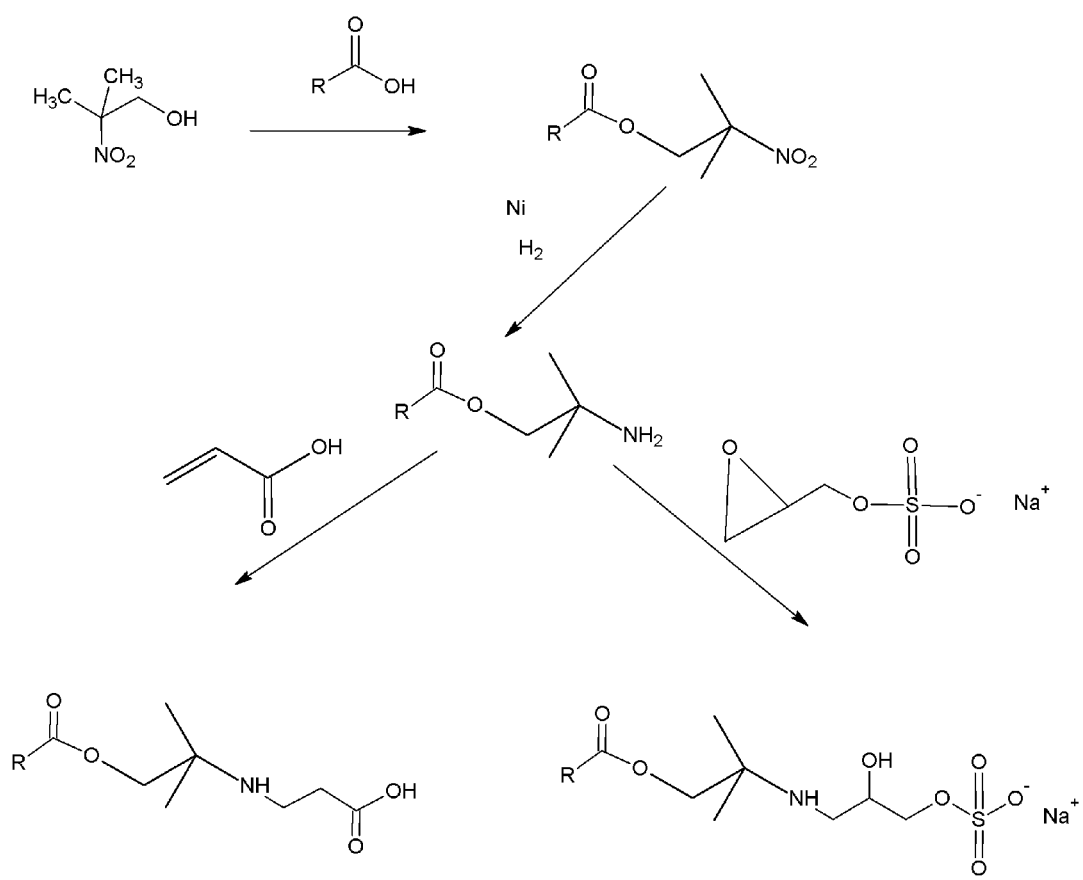

Another embodiment of the current invention is the synthesis of mild surfactants from nitroalcohols. FIGS. 31 through 33 teach the synthesis of these mild surfactants. Lower molecular weight acids produce lower foaming mild surfactants, whereas higher molecular weight carboxylic acids yield higher foam. Lauric acid is the preferred embodiment for a high foaming, mild surfact. Coconut fatty acid performs similarly, but at a lower cost. A good surfactant with low foam can be made using octanoic acid as the carboxylic acid.

Figure 34:
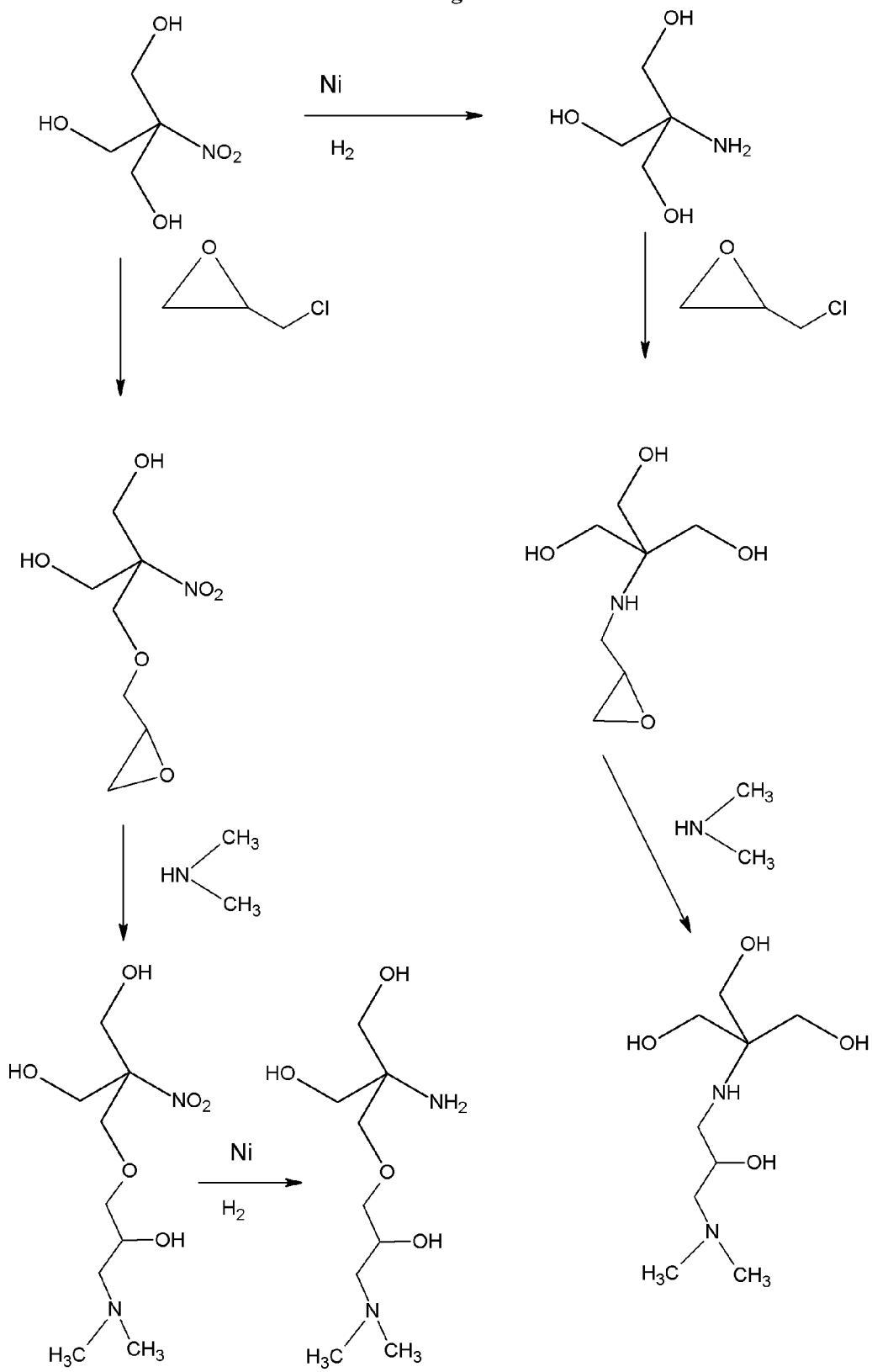
FIGS. 34-38 show the synthesis of polyamines from nitroalcohols.
Figure 35:
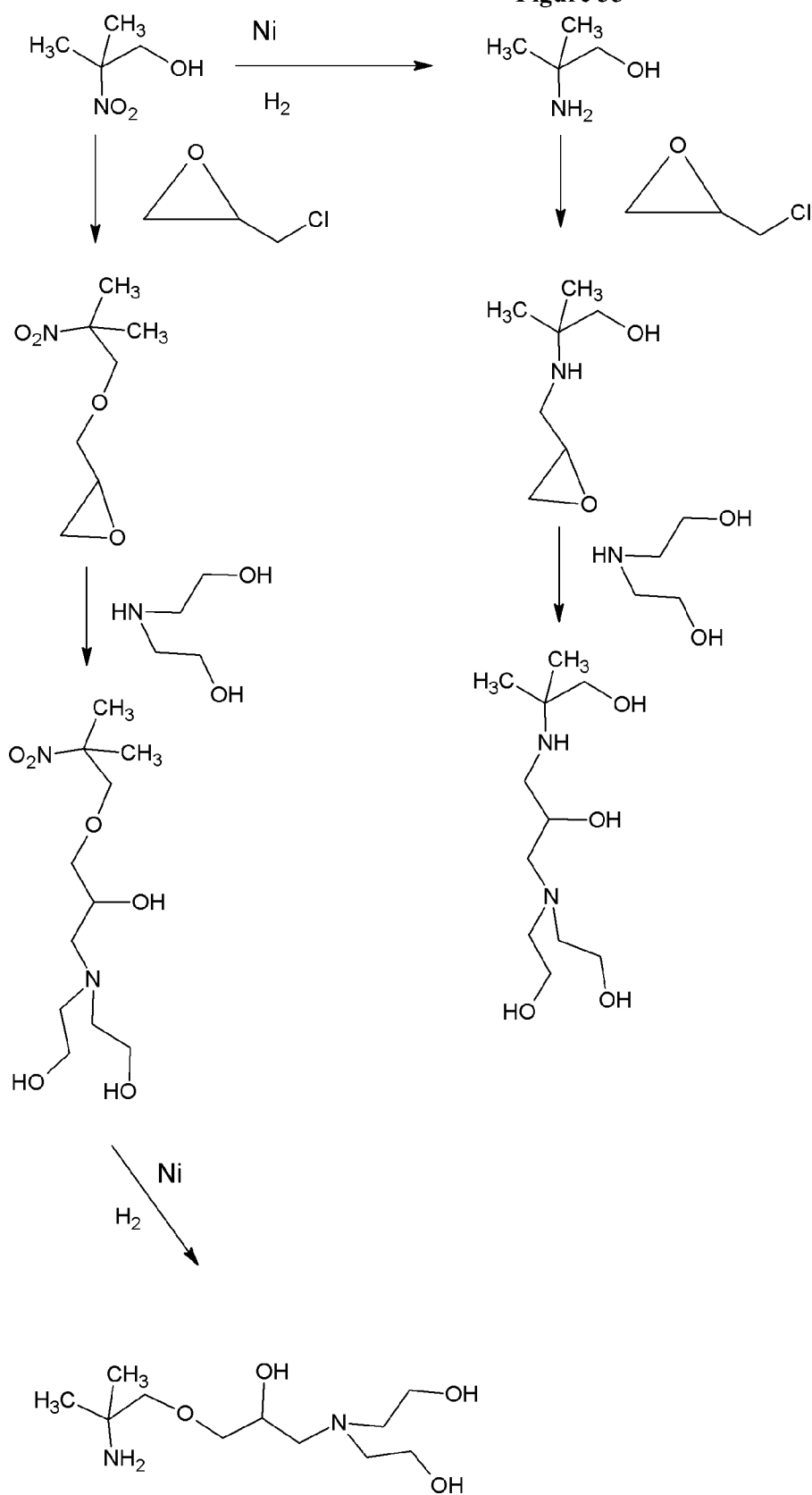
Figure 36:
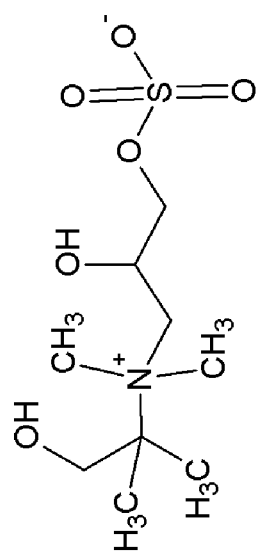
Figure 36:
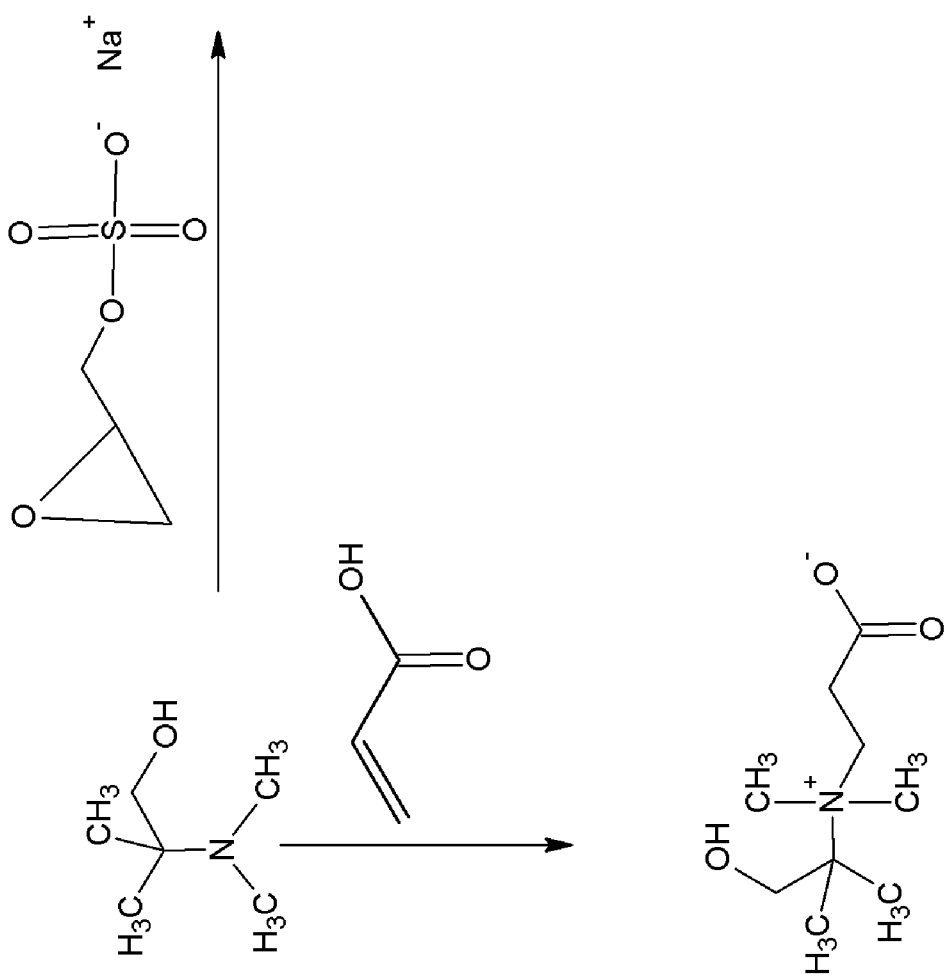
Figure 37:
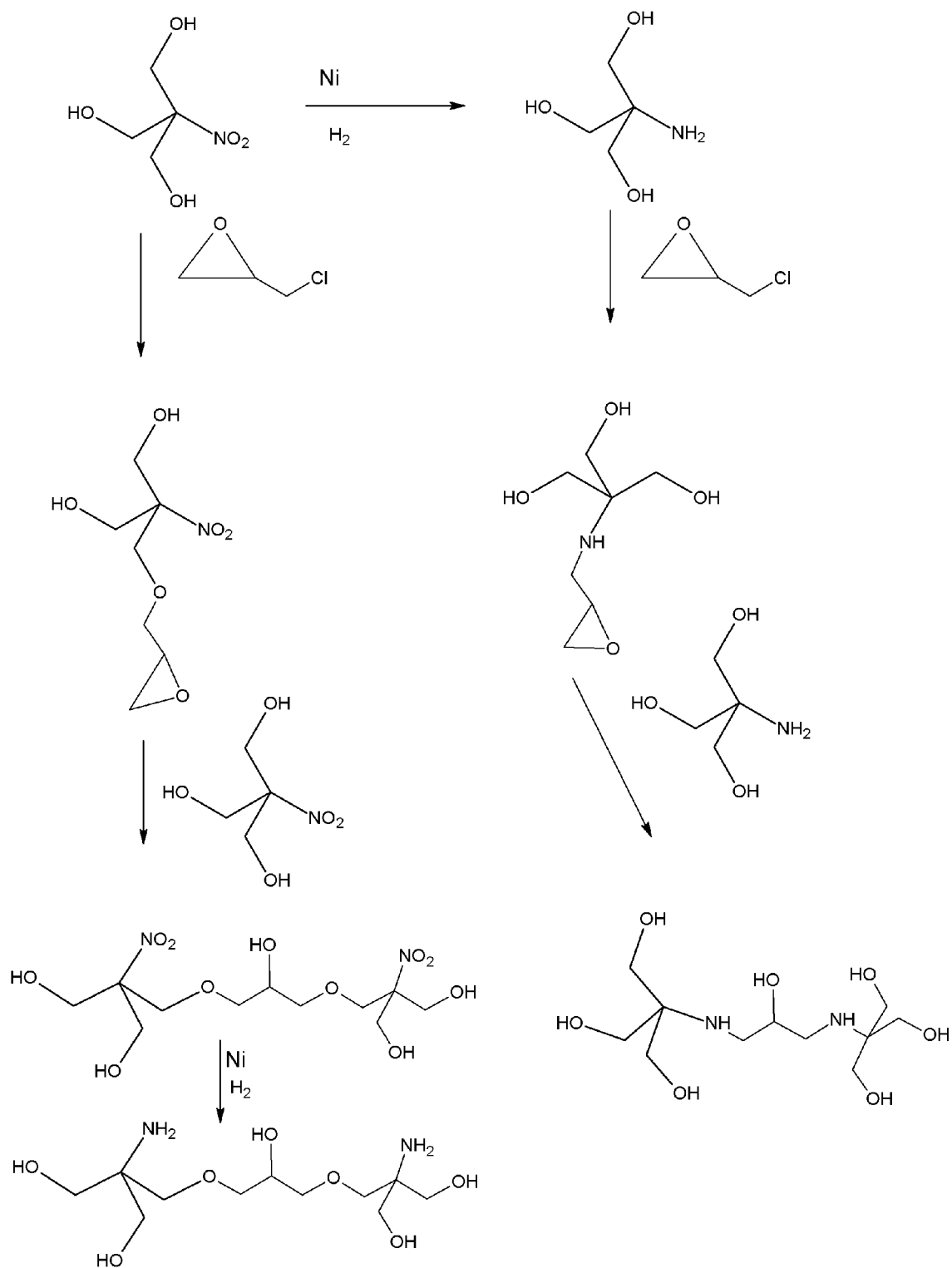
Figure 38:
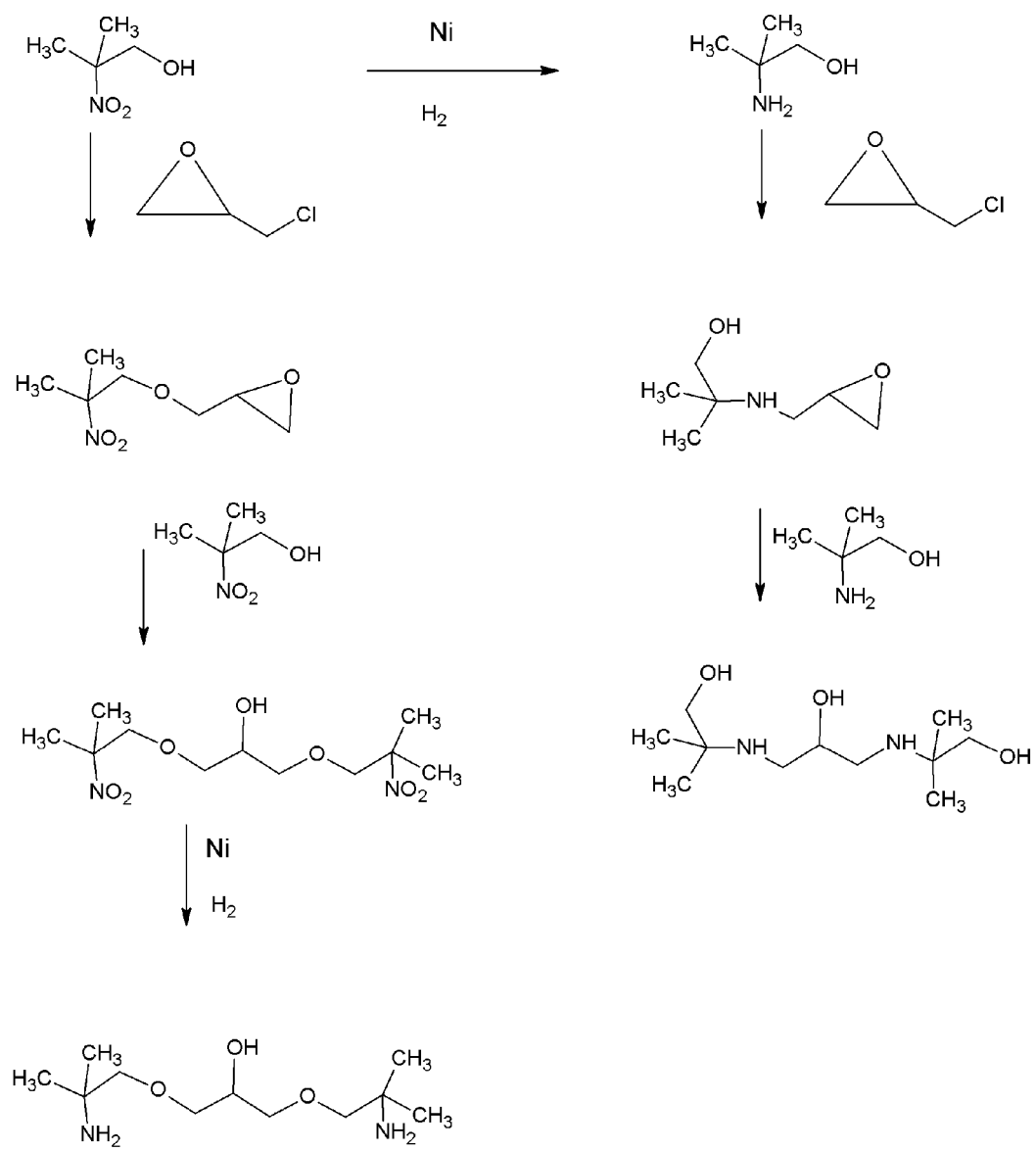

Another embodiment of the current invention is the synthesis of polyamines from nitroalcohols. FIGS. 34 and 35 teach the synthesis of diamines from nitroalcohols. FIG. 34 teaches the synthesis with several hydroxyl groups present. Additional amino groups can be added by reacting more than one equivalent of epichlorohydrin to the nitroalcohol, up to the number of hydroxyl groups, and then reacting the same number of equivalents of amine to the oxirane containing amine. In the case where the nitroalcohol is reduced to the amino alcohol in the beginning, the addition of base, such as caustic, to the amino alcohol will assist in the reaction of the epichlorohydrin with the hydroxyl groups. Without the base, the epichlorohydrin will preferably react with the amine as outlined in the 1 equivalent addition depicted in FIG. 34 and FIG. 35. FIG. 26 demonstrates that tertiary amines can be used to make zwitterionic buffers with quaternary amine functionality from tertiary amines. While not explicitly shown, any other tertiary amine can be used as the starting material and is part of the invention described herein. FIG. 37 and FIG. 38 demonstrate that diamines can be made from nitroalcohols by reacting sequentially the nitroalcohol with epichlorohydrin and then the second equivalent of the nitroalcohol, followed by reduction. Also taught is that a reduction step can take place in the beginning to yield a diamine with two secondary amino groups. The nitroalcohols or alkanolamines do not need to be symmetric, but others may be used in the synthesis of the diamine and is part of the invention disclosed herein.

As outlined earlier, the resulting amines can be reacted further with vinyl acids, monochloroacetic acid, sodium vinyl sulfonate, or an oxirane sulfonate to further add acidic character to the zwitterionic buffer.

Several descriptions and illustrations have been presented to enhance understanding of the present invention. One skilled in the art will know that numerous changes and variations are possible without departing from the spirit of the invention. Each of these changes and variations are within the scope of the present invention.

I claim:
1. A biological buffer of the following structure:

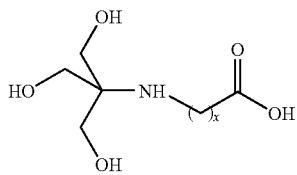

Where x is from 3 to 8.

2. A Biological Buffer of the following structure:

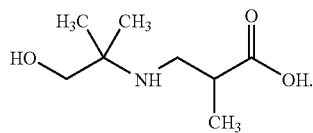

3. A Biological Buffer of the following structure:

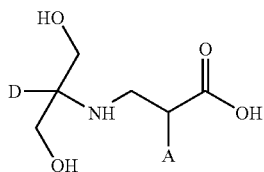

Where A is chosen from the group H, —OH, —CH$_3$, and —CH$_2$CH$_3$, and where D is from the group H, —CH$_3$, —CH$_2$CH$_3$.

4. A Biological Buffer of the following structure:

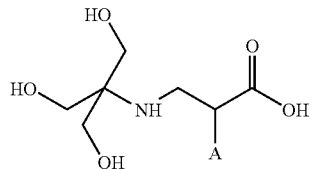

Where A is chosen from the group —OH, —CH$_3$, or —CH$_2$CH$_3$.

5. A Biological Buffer of claim 4 where A=—OH.
6. A Biological Buffer of claim 4 where A=—CH$_3$.
7. A Biological Buffer of the following structure:

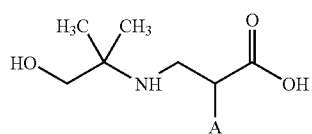

Where A is chosen from the group —H, —OH, or —CH$_2$CH$_3$.

8. A Biological Buffer of claim 7 where A=H.
9. A Biological Buffer of claim 7 where A=—OH.

* * * * *